(12) United States Patent
Sarwal et al.

(10) Patent No.: US 9,290,813 B2
(45) Date of Patent: Mar. 22, 2016

(54) BIOMARKERS FOR DETERMINING AN ALLOGRAFT TOLERANT PHENOTYPE

(75) Inventors: Minnie M. Sarwal, Portola Valley, CA (US); Li Li, Fremont, CA (US); Samuel Strober, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 553 days.

(21) Appl. No.: 13/512,539

(22) PCT Filed: Dec. 1, 2010

(86) PCT No.: PCT/US2010/058496
§ 371 (c)(1),
(2), (4) Date: Aug. 10, 2012

(87) PCT Pub. No.: WO2011/068829
PCT Pub. Date: Jun. 9, 2011

(65) Prior Publication Data
US 2012/0329668 A1 Dec. 27, 2012

Related U.S. Application Data

(60) Provisional application No. 61/283,393, filed on Dec. 2, 2009.

(51) Int. Cl.
*C12Q 1/68* (2006.01)
*C07H 21/04* (2006.01)

(52) U.S. Cl.
CPC ............ *C12Q 1/6883* (2013.01); *C12Q 1/6888* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,607,879 B1 | 8/2003 | Cocks et al. | |
| 7,026,121 B1 | 4/2006 | Wohlgemuth et al. | |
| 7,879,556 B2 | 2/2011 | Wohlgemuth et al. | |
| 2003/0017619 A1 | 1/2003 | Rokubo et al. | |
| 2003/0104371 A1 | 6/2003 | Strom et al. | |
| 2004/0163654 A1 | 8/2004 | Williams | |
| 2006/0088836 A1 | 4/2006 | Wohlgemuth et al. | |
| 2006/0088876 A1 | 4/2006 | Bauer | |
| 2006/0246485 A1 | 11/2006 | Sarwal et al. | |
| 2006/0269949 A1 | 11/2006 | Halloran et al. | |
| 2006/0281122 A1 | 12/2006 | Bryant et al. | |
| 2007/0031890 A1 | 2/2007 | Wohlgemuth et al. | |
| 2007/0111210 A1 | 5/2007 | Bigaud et al. | |
| 2007/0122806 A1 | 5/2007 | Strom et al. | |
| 2007/0134728 A1 | 6/2007 | Hu et al. | |
| 2007/0212701 A1 | 9/2007 | O'Toole et al. | |
| 2007/0232658 A1 | 10/2007 | Wagner et al. | |
| 2007/0264272 A1 | 11/2007 | Perreault et al. | |
| 2008/0233573 A1 | 9/2008 | Storm et al. | |
| 2009/0022730 A1 | 1/2009 | Raulf et al. | |
| 2009/0197286 A1 | 8/2009 | Karin et al. | |
| 2009/0269334 A1 | 10/2009 | Bigaud et al. | |
| 2009/0304705 A1 | 12/2009 | Grass | |
| 2010/0120629 A1 | 5/2010 | Ellis et al. | |
| 2011/0171645 A1* | 7/2011 | McManus et al. | ........... 435/6.11 |
| 2011/0201519 A1 | 8/2011 | Sarwal et al. | |
| 2013/0157888 A1 | 6/2013 | Nagele | |

FOREIGN PATENT DOCUMENTS

| | | |
|---|---|---|
| EP | 1731620 | 12/2006 |
| EP | 2295966 | 3/2011 |
| WO | 2004/074815 | 9/2004 |
| WO | 2005/005601 | 1/2005 |
| WO | 2005/070086 | 8/2005 |
| WO | 2007/104537 | 9/2007 |
| WO | 2007/121922 | 11/2007 |
| WO | 2008/009132 | 1/2008 |
| WO | 2008/084331 | 7/2008 |
| WO | 2009/143624 | 12/2009 |
| WO | 2010038974 | 8/2010 |

OTHER PUBLICATIONS

Nesslinger; et al., "A viral vaccine encoding prostate-specific antigen induces antigen spreading to a common set of self-proteins in prostate cancer patients", Clinical Cancer Research (Aug. 2010), 16(15):4046-4056.
Agilent-014850 whole human genome microarray 4x44K G4112F (Probe Name Version), GEO (2008), XP002594592.
Akalin; et al., "Gene expression analysis in human renal allograft biopsy samples using high-density oligoarray technology", Transplantation (2001), 72(5):948-53.
Brouard; et al., "Identification of a peripheral blood transcriptional biomarker panel associated with operational renal allograft tolerance", PNAS (2007), 104(39):15448-15453.
Carvalho-Gaspar; et al., "Chemokine gene expression during allograft rejection: Comparison of two quantitative PCR techniques", Journal of Immunological Methods (2005), 301(1-2):41-52.
Chan, "Integrating Transcriptomics and Proteomics", Drug Discovery and Development (2006), printed from www.ddmag.com, 6 pages.

(Continued)

*Primary Examiner* — Nancy T Vogel
(74) *Attorney, Agent, or Firm* — David C. Scherer; Bozicevic, Field & Francis, LLP

(57) ABSTRACT

Methods are provided for determining whether a subject has a graft tolerant phenotype. In practicing the subject methods, the expression level of one or more gene in a sample from the subject, e.g., a blood sample, is assayed to obtain a gene expression result, where the gene expression result includes a result for a biomarker of graft tolerance. The obtained gene expression result is then employed to determine whether the subject has a graft tolerant phenotype. Also provided are compositions, systems and kits that find use in practicing the subject methods. The methods and compositions find use in a variety of applications, including the determination of an immunosuppressive therapy regimen.

20 Claims, 5 Drawing Sheets

(56) References Cited

OTHER PUBLICATIONS

Chen; et al., "Discordant protein and mRNA expression in lung adenocarcinomas", Molecular and Cellular Proteomics (2002), 1(4):304-13.

Cheung; et al., "Natural Variation in Human Gene Expression Assessed in Lymphoblastoid Cells," Nature Genetics (2003), 33:422-425.

Chu; et al., "Cloning of a new "finger" protein gene (ZNF173) within the class I region of the human MHC", Genomics (1995), 29(1):229-39.

Chua; et al., "Applications of Microarrays to Renal Transplantation: Progress and Possibilities" Frontiers in Bioscience (2003), 8:S913-23.

Database Embl [Online], "Thymidine Kinase, Cytosolic (human), mRNA Sequence", (1998), 2pages, XP002434108, Database accession No. AA778098.

Dugré; et al., "Cytokine and cytotoxic molecule gene expression determined in peripheral blood mononuclear cells in the diagnosis of acute renal rejection.", Transplantation (2000), 70(7):1074-1080.

Enard; et al., "Intra- and interspecific variation in primate gene expression patterns", 296(5566):340-3.

Farivar; et al., "The role of CC and CXC chemokines in cardiac allograft rejection in rats", Experimental and Molecular Pathology (2005), 78(3):171-176.

Flechner; et al., "Kidney transplant rejection and tissue injury by gene profiling of biopsies and peripheral blood lymphocytes", American Journal of Transplantation (2004), 4(9):1475-89.

Fujiwaki; et al., "Thymidine Kinase in Epitheliai Ovarian Cancer: Relationship with the Other Pyrimidine Pathway Enzymes", Int. J. Cancer (2002), 99(3):328-335.

Gimino; et al., Gene Expression Profiling of Broncholveolar Lavage Cells in Acute Lung Rejection, American Journal of Respiratory and Critical Care Medicine (2003), 168:1237-1242.

Gronowitz; et al., "Serum Thymidine Kinase in Transplant Patients: Its Relation to Cytomegalovirus Activity, Renal Transplant Rejection and its Use for Monitoring of Antiviral Therapy," Annals of Clinical Research (1986), 18(2):71-75.

Hernandez-Fuentes; et al., "Immunologic monitoring", Immunological Reviews (2003), 196:247-264.

Horwitz; et al., "Detection of Cardiac Allograft Rejection and Response to Immunosuppressive Therapy with Peripheral Blood Gene Expression," Circulation (2004), 110:3815-3821.

Jevnikar; et al., "Late Kidney Allograft Loss: What We Know About It, and What We Can Do About It", Clin J Am Soc Nephrol (2008), 3(856-867).

Joosten; et al., "Chronic Renal Allograft Rejection: Pathophysiologic Considerations", Kidney International (2005), 68:1-13.

Lee et al., "Expression profiling of murine double-negative regularoty T cells suggest mechanisms for prolonged cardiac allograft survival", J. Immunol. (2005), 174(8):4535-4544.

Li; et al., "Identifying compartment-specific non-HLA targets after renal transplantation by integrating transcriptome and "antibodyome" measures", PNAS (2009), 106(11):4148-4153.

Mansfield; et al., "Arraying the Orchestration of Allograft Pathology", American Journal of Transplantation (2004), 4(6):853-62.

Marsden, "Predicting Outcomes after Renal Transplantation—New Tools and Old Tools," The New England Journal of Medicine (2003), 349(2):182-184.

Martinez-Llordella; et al., "Using transcriptional profiling to develop a diagnostic test of operational tolerance in liver transplant recipients", The Journal of Clinical Investigations (2008), 118(8):2845-2857.

Mcmorrow; et al., "New intra-renal graft genes associated with tolerance or rejection", Kidney International, symp. 1 (2002), 61: S85-S93.

Medbury; et al., "The Cytokine and Histological Response in Islet Xenograft Rejection is Dependent Upon Species Combination," Transplantation (1997), 64(9):1307-1314.

Midha; et al., "Chemokine Expression in Nerve Allografts," Neurosurgery (2004), 54(6):1472-149.

O'Riordan; et al., "Bioinformatic Analysis of the Urine Proteome of Acute Allograft Rejection," Journal of American Society of Nephrology (2004), 15:3240-3248.

Sarwal; et al., "Integrative Genomics to Identify Non-HLA Allogenic Kidney-Specific Targets after Kidney Transplantation", Transplantation (2008), 86(25):13, Oral Abstracts, downloaded Apr. 6, 2010.

Sarwal; et al., "Molecular Heterogeneity in Acute Renal Allograft Rejection Identified by DNA Microarray Profiling," New England Journal of Medicine (2003), 349:125-138.

Scherer; et al., "Early Prognosis of the Development of Renal Chronic Allograft Rejection by Gene Expression Profiling of Human Protocol Biopsies", Transplantation (2003), 75(8):1323-30.

Serody; et al., "T-lymphocyte production of macrophage inflammatory protein-lalpha is critical to the recruitment of CD8(+) T cells to the liver, lung, and spleen during graft-versus-host disease", Blood (2000), 96(9):2973-2980.

Shi; et al., "[Clinical significance of RANTES and MIP-1 alpha in acute rejection episode in kidney transplantation]", Zhongguo Yi Xue Ke Xue Yuan Xue Bao (2004), abstract.

Simon; et al., "Serial Peripheral Blood Perforin and Granzyme B Gene Expression Measurements for Prediction of Acute Rejection in Kidney Graft Recipients," American Journal of Transplantation (2003), 3:1121-1127.

Teramoto; et al., "DNA Synthesis in Hepatocytes During Liver Allograft Rejection in Rats", Transplantation (1990), 50(2):199-201.

Thomson; et al., "Monitoring the Patient Off Immunosuppression" Transplantation (2001), 72(8):S13-S22.

Wakui; et al., "Genes Highly Expressed in the Early Phase of Murine Graft-Versus-Host Reaction," Biochemical and Biophysical Communications (2001), 282:200-206.

Whitfield; et al., "Systemic and Cell Type-Specific Gene Expression Patterns in Scleroderma Skin," Proc. Natl. Acad Sci. (2003), 100(21):12319-12324.

Wu, "Analysing Gene Expression Data From DNA Microarrays to Identify Candidate Genes," Journal of Pathology (2001), 195:53-65.

Zhang; et al., "Microarray Analysis of Gene Expression in Peripheral Blood Mononuclear Cells Derived From Long-Surviving Renal Recipients", Transplantation Proceedings (2002), 34:1757-1759.

Alarcon; et al. "Time to renal disease and end-stage renal disease in PROFILE: a multiethnic lupus cohort", PLos Med (Oct. 2006), 3(10):e396.

Gwinner; et al. "Renal transplant rejection markers." World J Urol (Oct. 2007), 25(5):445-455.

Lang; et al. "DUSP meet immunology: dual specificity MAPK phosphatases in control of the inflammatory response", J Immunol (Dec. 2006), 177(11):7497-504.

Ling; et al. "Integrative urinary peptidomics in renal transplantation identifies biomarkers for acute rejection", J Am Soc Nephrol (Apr. 2010), 21(4):646-653.

Rotondi; et al. "High pretransplant serum levels of CXCL9 are associated with increased risk of acute rejection and graft failure in kidney graft recipients", Transpl Int (May 2010), 23(5):465-475.

Sigdel; et al. "Shotgun proteomics identifies proteins specific for acute renal transplant rejection", Proteomics Clin Appl (Jan. 2010), 4(1):32-47.

Voshol; et al. "Evaluation of biomarker discovery approaches to detect protein biomarkers of acute renal allograft rejection", J Proteome Res (Jul.-Aug. 2005), 4(4):1192-1199.

Roedder; et al., "The pits and pearls in translating operational tolerance biomarkers into clinical practice", Current Opinion in Organ Transplantation (Dec. 2012), 17(6):655-662.

Famulski; et al., "Changes in the Transcriptome in Allograft Rejection: IFN-.gamma.-Induced Transcripts in Mouse Kidney Allografts", American Journal of Transplantation (Jun. 2006), 6(6):1342-1354.

Akalin; et al., "Bocking Cell Microtubule Assembly Inhibits the Alloimmune Response In Vitro and Prolongs Renal Allograft Survival by Inhibition of Th1 and Sparing of Th2 Cell Function In Vivo", Journal of the American Society of Nephrology (1995), 5(7):1418-1425.

Braud; et al., "Immunosuppresive Drug-Free Operational Immune Tolerance in Human Kidney Transplant Recipients: Part 1. Blood

(56) References Cited

OTHER PUBLICATIONS

Gene Expression Statistical Analysis", Journal of Cellular Biochemistry (Apr. 2008),103(6):1681-1692.
Hauge; et al., "Characterization of the FAM110 gene family", Genomics (May 2007), 90:14-27.
Hillier; et al., "Generation and annotation of the DNA sequences of human chromosomes 2 and 4", Nature (2005), 434:724-731.
Matsuki; et al., "Novel regulation of MHC class II function in B cells", The EMBO Journal (Jan. 2007), 26:846-854.
Saint-Mezard; et al., "Analysis of independent microarray datasets of renal biopsies identifies a robust transcript signature of acute allograft rejection", Transplant International (Mar. 2009), 22(3):293-302.
"GeneChip 3' IVT PLUS Reagent Kit", Affymetrix (2013), User Manual, 45 pgs.
Communal; et al. "Reciprocal modulation of mitogen-activated protein kinases and mitogen-activated protein kinase phosphatase 1 and 2 in failing human myocardium", J Cardiac Failure (Apr. 2002), 8(2):86-92.
"Affymetrix Human Genome U133 Plus 2.0 Array", Gene Expression Omnibus (Nov. 2003), XP002627319, 3 pgs.
Al-Lamki; et al., "Expression of Tumor Necrosis Factor Receptors in Normal Kidney and Rejecting Renal Transplants", Laboratory Investigation (Nov. 2001), 81(11):1503-1515.
Chen; et al., "Differentially Expressed RNA from Public Microarray Data Identifies Serum Protein Biomarkers for Cross-Organ Transplant Rejection and Other Conditions", PLOS Computational Biology (Sep. 2010), 6(9):e1000940.
Hardiman, "Microarray platforms—comparisons and contrasts", Pharmacogenomics (Jan. 2004), 5(5): 487-502.
Hauser; et al., "Prediction of Acute Renal Allograft Rejection by Urinary Monokine Induced by IFN-gamma (MIG)", The American Society of Nephrology (Jan. 2005), 16(6):1849-1858.
Hidalgo; et al., "The Transcriptome of Human Cytotoxic T Cells: Measuring the Burden of CTL-Associated Transcripts in Human Kidney Transplants", American Journal of Transplantation (Mar. 2008), 8(3):637-646.
Mengel; et al., "Scoring Total Inflammation Is Superior to the Current Banff Inflammation Score in Predicting Outcome and the Degree of Molecular Disturbance in Renal Allografts", American Journal of Transplantation (Aug. 2009), 9(8):1859-1867.
Morgun; et al., "Molecular Profiling Improves Diagnoses of Rejected and Infection in Transplanted Organs", Circulation Research (Jun. 2006), 98(12):e74-83.
Li; et al., "A Peripheral Blood Diagnostic Test for Acute Rejection in Renal Transplantation", American Journal of Transplantation (Oct. 2012), 12(10):2710-2718.
Butte; et al., "Protein microarrays discover angiotensinogen and PRKRIP1 as novel targets for autoantibodies in chronic renal disease", Mol Cell Proteomics (Mar. 2011), 10(3):M110.000497.
Cox; et al., "Altered modulation of WNT-beta-catenin and PI3K/Akt pathways in IgA nephropathy", Kidney Int (Aug. 2010), 78(4):396-407.
Dinarello; et al., "Anti-inflammatory Agents: Present and Future", Cell (Mar. 2010), 140(6):935-950.
Ismail; et al., "Important fluorinated drugs in experimental and clinical use", Journal of Fluorine Chemistry (Dec. 2002), 118(1):27-33.
Kalil; et al., "Meta-analysis: the efficacy of strategies to prevent organ disease by cytomegalovirus in solid organ transplant recipients", Ann Intern Med (Dec. 2005), 143(12):870-880.
Kaposztas; et al., "Impact of rituximab therapy for treatment of acute humoral rejection", Clin Transplant (Jan.-Feb. 2009), 23(1):63-73.
Metz; et al., "Application of proteomics in the discovery of candidate protein biomarkers in a diabetes autoantibody standardization program sample subset", J Proteome Res (Feb. 2008), 7(2):698-707.
Sato; et al., "Aberrant CD3- and CD3-mediated signaling events in cord blood T Cells are associated with dysfunctional regulation of Fas ligand-mediated cytotoxicity", The Journal of Immunology (Apr. 1999), 162 (8):4464-4471.
Sigdel; et al., "Profiling of autoantibodies in IgA nephropathy, an integrative antibiomics approach", Clin J Am Soc Nephrol (Dec. 2011), 6(12):2775-2784.
Gerrits; et al., "Donor-reactive cytokine production after HLA-identical living related kidney transplantation: a protein-array analysis", (Nov. 2006), 38(9):2825-7.
Joosten; et al., "Antibody response against the glomerular basement membrane protein agrin in patients with transplant glomerulopathy", American Journal of Transplantation (Feb. 2005), 5(2):383-93.
Mizutani; et al., "Frequency of MIC antibody in rejected renal transplant patients without HLA antibody", Human Immunology (Mar. 2006), 67(3):223-9.
Kazutoshi Takahashi et al: "Induction of Pluripotent Stem Cells from Adult Human Fibroblasts by Defined Factors", Cell, Cell Press, US, vol. 131, No. 5, Nov. 30, 2007, pp. 861-872.

\* cited by examiner

# BIOMARKERS FOR DETERMINING AN ALLOGRAFT TOLERANT PHENOTYPE

INTRODUCTION

Transplantation of a graft organ or tissue from a donor to a host patient is a feature of certain medical procedures and treatment protocols. Despite efforts to avoid graft rejection through host-donor tissue type matching, in transplantation procedures where a donor organ is introduced into a host, immunosuppressive therapy is generally required to the maintain viability of the donor organ in the host.

A variety of immunosuppressive agents have been employed in transplantation procedures, including azathioprine, methotrexate, cyclophosphamide, FK-506, rapamycin and corticosteroids. Agents finding increased use in immunosuppressive therapy due to their preferential effect on T-cell mediated reactions are the cyclosporins.

Following transplantation, administration of the immunosuppressive agent must be continued indefinitely since the benefits of immunosuppressive therapy are reversible and graft rejection may occur once administration of the immunosuppressive agent is discontinued. While use of immunosuppressive agents, such as Cyclosporin A, has been reported to prolong the survival of allogeneic transplants involving skin, heart, kidney, pancreas, bone marrow, small intestine and lung, use of such agents is not without undesirable side effects. Examples of undesirable side effects include increased risk of development of neoplastic disease conditions, e.g., skin cancer, lymphoma, etc.

While most recipients who discontinue their immunosuppressive treatment following a graft go on to suffer rejection, not all subjects suffer graft rejection. In a few cases, individuals tolerate their graft without immunosuppression, suggesting that immune non-responsiveness can be achieved in clinical practice. The mechanisms of this process are not well understood, but may involve a combination of clonal deletion, clonal anergy and the generation of active regulatory T cells.

Because of the undesirable sides effects and risks of long term immunosuppressive therapy, it would be desirable to be able identify those individuals who are tolerant to their graft, i.e., graft tolerant (TOL), so that immunosuppression could be reduced or even discontinued in those individuals. Of particular interest would be the development of a way to identify graft tolerant individuals without first discontinuing immunosuppressive therapy, thereby avoiding the risk of graft rejection and damage to the graft associated therewith. The present invention meets this, and other, needs.

SUMMARY OF THE INVENTION

Methods are provided for determining whether a subject has a graft tolerant phenotype (TOL). In practicing the subject methods, the expression of at least one gene in a sample from the subject, e.g., a blood sample, is assayed to obtain an expression evaluation for the at least one gene. The obtained expression evaluation is then employed to determine whether the subject has a graft tolerant phenotype. Also provided are compositions, systems and kits that find use in practicing the subject methods. The subject methods and compositions find use in a variety of applications, including the determination of an immunosuppressive therapy regimen.

DESCRIPTION OF THE SPECIFIC EMBODIMENTS

Figure 1:
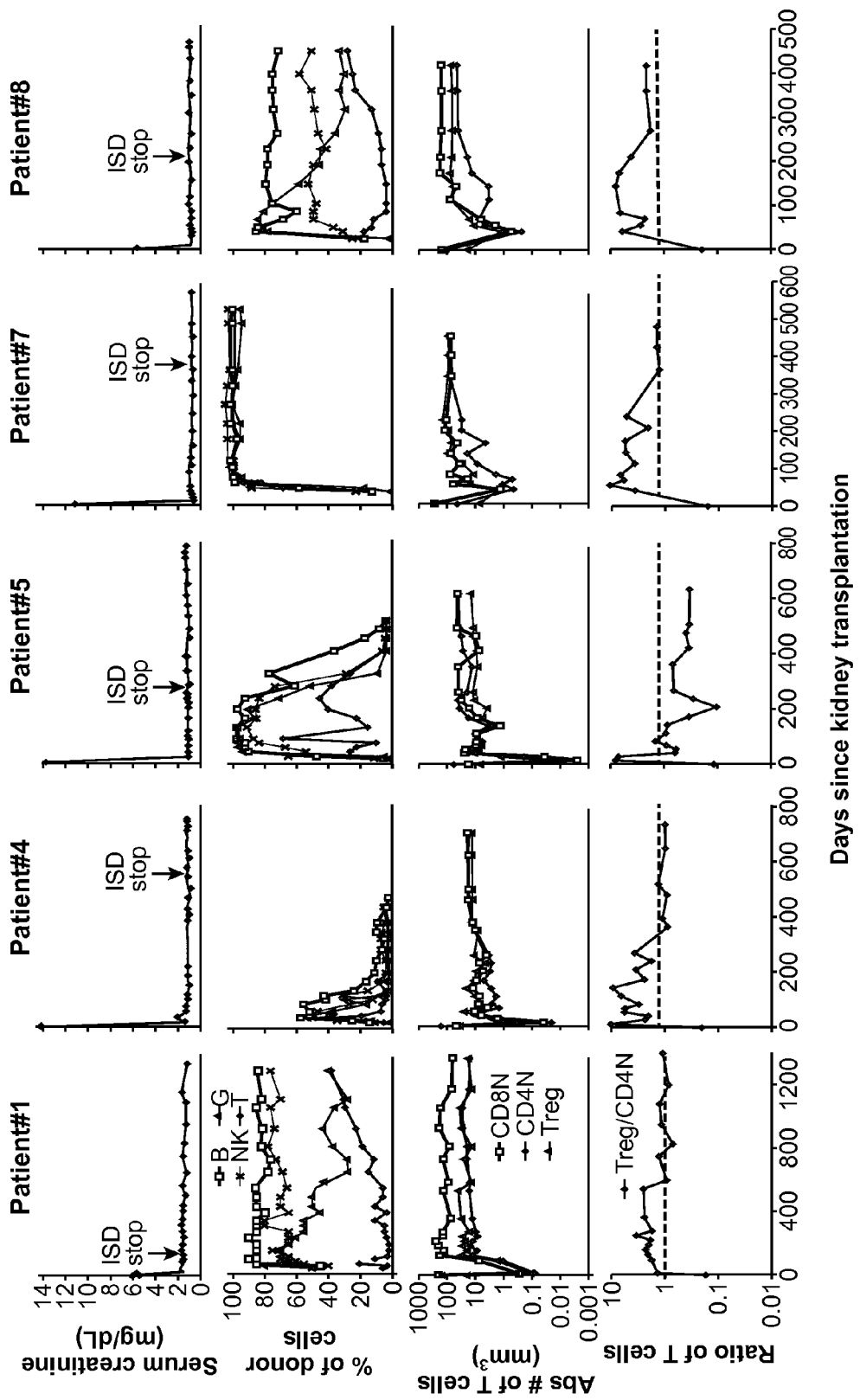
FIG. 1. Serum creatinine concentrations, chimerism, and T cell subsets in patients who stopped anti-rejection immunosuppressive drugs (ISD). Top panels show serum creatinine concentrations at serial time points in patients #1, 4, 5, 7, and 8. Arrows show time points at which immunosuppressive drugs were stopped. The percentages of donor type cells measured by STR analysis among enriched blood T, B, NK cells and granulocytes (G) are shown for all patients. The two bottom panels show the changes in the absolute numbers and ratios of blood T cell subsets including CD8+ naïve T cells (CD8N), CD4+ naïve T cells (CD4N), and CD4+CD25+ T cells (Treg cells. Ratios of the absolute numbers of Treg cells to CD4+ naïve T cells (Treg/CD4N) are also shown. Treg cells were >80% FoxP3+ using the CD25+ threshold for Treg identification. The first posttransplant time point for T cell subsets was delayed in some patients due to lymphopenia.

Methods are provided for determining whether a subject has a graft tolerant phenotype. In practicing the subject methods, the expression of at least one gene in a sample from the subject, e.g., a blood sample, is assayed to obtain an expression evaluation for the at least one gene. The obtained expression evaluation is then employed to determine whether the subject has a graft tolerant phenotype. Also provided are compositions, systems and kits that find use in practicing the subject methods. The methods and compositions find use in a variety of applications, including the determination of an immunosuppressive therapy regimen.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the subject invention is directed to methods of determining whether a subject has a graft tolerant phenotype, as well as reagents and kits for use in practicing the subject methods. In further describing the invention, the subject methods are described first, followed by a review of the reagents and kits for use in practicing the subject methods.

Methods of Determining Whether a Subject has a Graft Tolerant Phenotype

Aspects of the subject invention provide methods of determining whether a patient or subject has a graft tolerant phenotype. By graft tolerant phenotype is meant that the subject does not reject a graft organ, tissue or cell(s) that has been introduced into/onto the subject. In other words, the subject tolerates or maintains the organ, tissue or cell(s) that has been transplanted to it. As in known in the transplantation field, the graft organ, tissue or cell(s) may be allogeneic or xenogeneic, such that the grafts may be allografts or xenografts. A feature of the graft tolerant phenotype detected or identified by the subject methods is that it is a phenotype which occurs without immunosuppressive therapy, i.e., it is present in a host that is not undergoing immunosuppressive therapy such that immunosuppressive agents are not being administered to the host.

In practicing the subject methods, a subject or patient sample, e.g., cells or collections thereof, e.g., tissues, is assayed to determine whether the host from which the assayed sample was obtained is graft tolerant, i.e., has a graft tolerant phenotype. Accordingly, the first step of the subject methods is to obtain a suitable sample from the subject or patient of interest, i.e., a patient on immunosuppressive therapy and having at least one graft, e.g., allograft. The sample is derived from any initial suitable source, where sample sources of interest include, but are not limited to, many different physiological sources, e.g., CSF, urine, saliva, tears, tissue derived samples, e.g., homogenates, and blood or derivatives thereof.

In certain embodiments, a suitable initial source for the patient sample is blood. As such, the sample employed in the subject assays of these embodiments is generally a blood-derived sample. The blood derived sample may be derived from whole blood or a fraction thereof, e.g., serum, plasma, etc., where in many embodiments the sample is derived from blood cells harvested from whole blood. Of particular interest as a sample source are peripheral blood lymphocytes (PBL). Any convenient protocol for obtaining such samples may be employed, where suitable protocols are well known in the art.

In practicing the subject methods, the sample is assayed to obtain an expression evaluation, e.g., expression profile or expression signature, for one or more genes, where the term expression profile (or expression signature) is used broadly to include a genomic expression profile, e.g., an expression profile of nucleic acid transcripts, e.g., mRNAs, of the one or more genes of interest, or a proteomic expression profile, e.g., an expression profile of one or more different proteins, where the proteins/polypeptides are expression products of the one or more genes of interest. As such, in certain embodiments the expression of only one gene is evaluated. In yet other embodiments, the expression of two or more, e.g., about 5 or more, about 10 or more, about 15 or more, about 25 or more, about 50 or more, about 100 or more, about 200 or more, etc., genes is evaluated. Accordingly, in the subject methods, the expression of at least one gene in a sample is evaluated. In certain embodiments, the evaluation that is made may be viewed as an evaluation of the transcriptome, as that term is employed in the art. See e.g., Gomes et al., Blood (2001 Jul. 1) 98(1):93-9.

In many embodiments, a sample is assayed to generate an expression profile (or signature) that includes expression data for at least one gene/protein, usually a plurality of genes/proteins, where by plurality is meant at least two different genes/proteins, and often at least about 5, at least about 10, at least about 20 different genes/proteins or more, such as 50 or more, 100 or more, etc.

In the broadest sense, the expression evaluation may be qualitative or quantitative. As such, where detection is qualitative, the methods provide a reading or evaluation, e.g., assessment, of whether or not the target analyte, e.g., nucleic acid or expression product, is present in the sample being assayed. In yet other embodiments, the methods provide a quantitative detection of whether the target analyte is present in the sample being assayed, i.e., an evaluation or assessment of the actual amount or relative abundance of the target analyte, e.g., nucleic acid in the sample being assayed. In such embodiments, the quantitative detection may be absolute or, if the method is a method of detecting two or more different analytes, e.g., target nucleic acids, in a sample, relative. As such, the term "quantifying" when used in the context of quantifying a target analyte, e.g., nucleic acid(s), in a sample can refer to absolute or to relative quantification. Absolute quantification may be accomplished by inclusion of known concentration(s) of one or more control analytes and referencing the detected level of the target analyte with the known control analytes (e.g., through generation of a standard curve). Alternatively, relative quantification can be accomplished by comparison of detected levels or amounts between two or more different target analytes to provide a relative quantification of each of the two or more different analytes, e.g., relative to each other.

In certain embodiments, genes/proteins of interest are genes/proteins that are differentially expressed or present at different levels in graft tolerant versus non-graft tolerant individuals who have received a kidney allograft. Representative genes/proteins of interest in these embodiments include, but are not limited to, the genes/proteins provided in Table 1A, where the Entrez Gene ID number for each gene is listed. (Note that detailed information for each gene in Table 1A, including nucleotide sequence information, can be retrieved through the NCBI Entrez nucleotide database located at the website http (colon) //www (dot) ncbi.nlm.nih (dot) gov/nucleotide by selecting "Gene" as the database and entering the Entrez Gene ID number listed into the search window.)

In certain embodiments, at least one of the genes/proteins in the expression profile is from Table 1A, where the expression profile may include expression data for any combination of the genes listed in Table 1A (e.g., 1, 2, 3, 4, 5, 6, 7, 8, 9, 10, 11, 12, etc., up to and including all 21 genes in Table 1A).

TABLE 1A

A list of 21 genes whose expression level can be used to determine a TOL phenotype in a subject having a kidney transplant.

| Gene Symbol | Gene Information | Entrez Gene ID |
|---|---|---|
| BNC2 | Name: basonuclin 2 [*Homo sapiens*]<br>Other Aliases: RP11-183I6.1, BSN2, DKFZp686A01127, FLJ20043, FLJ34928<br>Chromosome: 9; Location: 9p22.3-p22.2<br>Annotation: Chromosome 9, NC_000009.11<br>(16409501 . . . 16870786, complement)<br>MIM: 608669 | 54796 |
| C1QC | Name: complement component 1, q subcomponent, C chain [*Homo sapiens*]<br>Other Aliases: C1Q-C, C1QG, FLJ27103<br>Other Designations: OTTHUMP00000002933; complement C1q subcomponent subunit C; complement component 1, q subcomponent, gamma polypeptide<br>Chromosome: 1; Location: 1p36.11<br>Annotation: Chromosome 1, NC_000001.10<br>(22970118 . . . 22974603)<br>MIM: 120575 | 714 |
| CCL4 | Name: chemokine (C-C motif) ligand 4 [*Homo sapiens*]<br>Other Aliases: ACT2, AT744.1, G-26, LAG1, MGC104418, MGC126025, MGC126026, MIP-1-beta, MIP1B, MIP1B1, SCYA2, SCYA4<br>Other Designations: CC chemokine ligand 4; chemokine C-C motif ligand 4; lymphocyte-activation gene 1; secreted protein G-26; small inducible cytokine A4 (homologous to mouse Mip-1b)<br>Chromosome: 17; Location: 17q12<br>Annotation: Chromosome 17, NC_000017.10 | 6351 |

TABLE 1A-continued

A list of 21 genes whose expression level can be used to determine
a TOL phenotype in a subject having a kidney transplant.

| Gene Symbol | Gene Information | Entrez Gene ID |
|---|---|---|
| | (34431220 . . . 34433014) MIM: 182284 | |
| CYP1B1 | Name: cytochrome P450, family 1, subfamily B, polypeptide 1 [Homo sapiens] Other Aliases: CP1B, GLC3A, P4501B1 Other Designations: OTTHUMP00000201401; aryl hydrocarbon hydroxylase; cytochrome P450, subfamily I (dioxin-inducible), polypeptide 1 (glaucoma 3, primary infantile); flavoprotein-linked monooxygenase; microsomal monooxygenase; xenobiotic monooxygenase Chromosome: 2; Location: 2p21 Annotation: Chromosome 2, NC_000002.11 (38294746 . . . 38303323, complement) MIM: 601771 | 1545 |
| FAM110C | Name: family with sequence similarity 110, member C [Homo sapiens] Other Designations: hypothetical protein LOC642273 Chromosome: 2; Location: 2p25.3 Annotation: Chromosome 2, NC_000002.11 (41608 . . . 46385, complement) MIM: 611395 | 642273 |
| GDEP | Gene description: gene differentially expressed in prostate [Homo sapiens] Chromosome: 4; Location: 4q21.1 Other Aliases: PCAN1 | 118425 |
| IGFL2 | Name: IGF-like family member 2 [Homo sapiens] Other Aliases: UNQ645, VPRI645 Other Designations: insulin growth factor-like family member 2 Chromosome: 19; Location: 19q13.32 Annotation: Chromosome 19, NC_000019.9 (46651039 . . . 46664561) MIM: 610545 | 147920 |
| IGH@ | Name: immunoglobulin heavy locus [Homo sapiens] Other Aliases: DKFZp686C15213, IGH, IGH.1@, IGHDY1, MGC72071, MGC88774 Other Designations: immunglobulin heavy chain variable region Chromosome: 14; Location: 14q32.33 | 3492 |
| IGHA2 | Name: immunoglobulin heavy constant alpha 2 (A2m marker) [Homo sapiens] Chromosome: 14; Location: 14q32.33 Annotation: Chromosome 14, NC_000014.8 (106053244 . . . 106054731, complement) MIM: 147000 | 3494 |
| IGHG4 | Official Symbol IGHG4 and Name: immunoglobulin heavy constant gamma 4 (G4m marker) [Homo sapiens] Other Aliases: MGC117419 Chromosome: 14; Location: 14q32.33 Annotation: Chromosome 14, NC_000014.8 (106090707 . . . 106092402, complement) MIM: 147130 | 3503 |
| IGJ | Name: immunoglobulin J polypeptide, linker protein for immunoglobulin alpha and mu polypeptides [Homo sapiens] Other Aliases: IGCJ, JCH Other Designations: immunoglobulin J chain Chromosome: 4; Location: 4q21 Annotation: Chromosome 4, NC_000004.11 (71521258 . . . 71532348, complement) MIM: 147790 | 3512 |
| KLF6 | Name: Kruppel-like factor 6 [Homo sapiens] Other Aliases: RP11-184A2.1, BCD1, CBA1, COPEB, CPBP, DKFZp686N0199, GBF, PAC1, ST12, ZF9 Other Designations: GC-rich binding factor; Kruppel-like zinc finger protein Zf9; core promoter element binding protein; protooncogene B-cell derived 1; suppression of tumorigenicity 12 (prostate) Chromosome: 10; Location: 10p15 Annotation: Chromosome 10, NC_000010.10 (3821234 . . . 3827455, complement) MIM: 602053 | 1316 |
| NXF3 | Name: nuclear RNA export factor 3 [Homo sapiens] Other Aliases: LL0XNC01-221F2.3 Chromosome: X; Location: Xq22-q23 Annotation: Chromosome X, NC_000023.10 | 56000 |

TABLE 1A-continued

A list of 21 genes whose expression level can be used to determine a TOL phenotype in a subject having a kidney transplant.

| Gene Symbol | Gene Information | Entrez Gene ID |
|---|---|---|
| | (102330749 ... 102348022, complement) MIM: 300316 | |
| PRAMEF3 | Name: PRAME family member 3 [*Homo sapiens*] Other Aliases: RP11-248D7.1 Chromosome: 1; Location: 1p36.21 Annotation: Chromosome 1, NC_000001.10 (13328196 ... 13331692, complement) | 401940 |
| RLBP1L1 | Name: clavesin 1 [*Homo sapiens*] Other Aliases: CRALBPL, FLJ37248, MGC34646, RLBP1L1 Other Designations: retinaldehyde binding protein 1-like 1 Chromosome: 8; Location: 8q12.3 Annotation: Chromosome 8, NC_000008.10 (62200525 ... 62414204) MIM: 611292 | 157807 |
| SHCBP1 | Name: SHC SH2-domain binding protein 1 [*Homo sapiens*] Other Aliases: FLJ22009, MGC26900, PAL Chromosome: 16; Location: 16q11.2 Annotation: Chromosome 16, NC_000016.9 (46614466 ... 46655311, complement) MIM: 611027 | 79801 |
| SPC25 | Name: SPC25, NDC80 kinetochore complex component, homolog (*S. cerevisiae*) [*Homo sapiens*] Other Aliases: AD024, MGC22228, SPBC25 Other Designations: 2600017H08Rik; kinetochore protein Spc25; spindle pole body component 25; spindle pole body component 25 homolog Chromosome: 2; Location: 2q31.1 Annotation: Chromosome 2, NC_000002.11 (169727401 ... 169746944, complement) MIM: 609395 | 57405 |
| TFDP3 | Name: transcription factor Dp family, member 3 [*Homo sapiens*] Other Aliases: RP3-358H7.2, CT30, DP4, E2F-like, HCA661, MGC161639 Other Designations: OTTHUMP00000024051; cancer/testis antigen 30 Chromosome: X; Location: Xq26.2 Annotation: Chromosome X, NC_000023.10 (132350697 ... 132352376, complement) MIM: 300772 | 51270 |
| TNFRSF17 | Name: tumor necrosis factor receptor superfamily, member 17 [*Homo sapiens*] Other Aliases: BCM, BCMA, CD269 Other Designations: B cell maturation antigen; B-cell maturation factor Chromosome: 16; Location: 16p13.1 Annotation: Chromosome 16, NC_000016.9 (12058964 ... 12061925) MIM: 109545 | 608 |
| UHRF1 | Name: ubiquitin-like with PHD and ring finger domains 1 [*Homo sapiens*] Other Aliases: FLJ21925, ICBP90, MGC138707, Np95, RNF106, hNP95 Other Designations: E3 ubiquitin-protein ligase UHRF1; RING finger protein 106; inverted CCAAT box-binding protein of 90 kDa; nuclear zinc finger protein Np95; transcription factor ICBP90; ubiquitin-like, containing PHD and RING finger domains, 1 Chromosome: 19; Location: 19p13.3 Annotation: Chromosome 19, NC_000019.9 (4909510 ... 4962165) MIM: 607990 | 29128 |
| VN1R2 | Name: vomeronasal 1 receptor 2 [*Homo sapiens*] Other Aliases: V1RL2 Other Designations: V1R-like 2; pheromone receptor Chromosome: 19; Location: 19q13.42 Annotation: Chromosome 19, NC_000019.9 (53761545 ... 53762855) | 317701 |

In certain embodiments, genes/proteins of interest are genes/proteins that are differentially expressed or present at different levels in graft tolerant versus non-graft tolerant individuals who have received a liver allograft (e.g., pediatric patients). Representative genes/proteins of interest in these embodiments include, but are not limited to, the genes/proteins provided in Table 1B, where the Entrez Gene ID number for each gene is listed. (Note that detailed information for each gene in Table 1B, including nucleotide sequence information, can be retrieved through the NCBI Entrez nucleotide database located at the website http (colon) //www (dot) ncbi.nlm.nih (dot) gov/ nucleotide by selecting "Gene" as the database and entering the Entrez Gene ID number listed into the search window.)

In certain embodiments, at least one of the genes/proteins in the expression profile is from Table 1B, where the expression profile may include expression data for any combination of the genes listed in Table 1B (e.g., 1, 2, 3, 4, 5, 6, 7, 8, 9, 10, 11, up to and including all 12 genes in Table 1B).

TABLE 1B

A list of 12 genes whose expression level can be used to determine a TOL phenotype in a subject having a liver transplant.

| Gene Symbol | Gene Information | Entrez Gene ID |
|---|---|---|
| AKR1C3 | Official Symbol AKR1C3 and Name: aldo-keto reductase family 1, member C3 (3-alpha hydroxysteroid dehydrogenase, type II) [Homo sapiens] Other Aliases: DD3, DDX, HA1753, HAKRB, HAKRe, HSD17B5, KIAA0119, hluPGFS Other Designations: aldo-keto reductase family 1, member C3; chlordecone reductase; dihydrodiol dehydrogenase 3; dihydrodiol dehydrogenase X; hydroxysteroid (17-beta) dehydrogenase 5; prostaglandin F synthase; trans-1,2-dihydrobenzene-1,2-diol dehydrogenase; type II 3a-hydroxysteroid dehydrogenase; type IIb 3-alpha hydroxysteroid dehydrogenase Chromosome: 10; Location: 10p15-p14 Annotation: Chromosome 10, NC_000010.10 (5136568 . . . 5149878) MIM: 603966 | 8644 |
| ASPH | Official Symbol ASPH and Name: aspartate beta-hydroxylase [Homo sapiens] Other Aliases: AAH, BAH, CASQ2BP1, HAAH, JCTN, junctin Other Designations: A beta H-J-J; aspartyl/asparaginyl-beta-hydroxylase; cardiac junctin; humbug; junctate; peptide-aspartate beta-dioxygenase Chromosome: 8; Location: 8q12.1 Annotation: Chromosome 8, NC_000008.10 (62413115 . . . 62627199, complement) MIM: 600582 | 444 |
| ERBB2 | Official Symbol ERBB2 and Name: v-erb-b2 erythroblastic leukemia viral oncogene homolog 2, neuro/glioblastoma derived oncogene homolog (avian) [Homo sapiens] Other Aliases: CD340, HER-2, HER-2/neu, HER2, NEU, NGL, TKR1 Other Designations: c-erb B2/neu protein; erbB-2; herstatin; neuroblastoma/glioblastoma derived oncogene homolog; v-erb-b2 avian erythroblastic leukemia viral oncogene homolog 2 (neuro/glioblastoma derived oncogene homolog) Chromosome: 17; Location: 17q21.1 Annotation: Chromosome 17, NC_000017.10 (37844393 . . . 37884915) MIM: 164870 | 2064 |
| FEM1C | Official Symbol FEM1C and Name: fem-1 homolog c (C. elegans) [Homo sapiens] Other Aliases: EUROIMAGE686608, EUROIMAGE783647, FEM1A, KIAA1785 Other Designations: feminization 1 homolog a Chromosome: 5; Location: 5q22 Annotation: Chromosome 5, NC_000005.9 (114856608 . . . 114880591, complement) MIM: 608767 | 56929 |
| MAFG | Official Symbol MAFG and Name: v-maf musculoaponeurotic fibrosarcoma oncogene homolog G (avian) [Homo sapiens] Other Aliases: MGC13090, MGC20149 Other Designations: basic leucine zipper transcription factor MafG; transcription factor MafG; v-maf musculoaponeurotic fibrosarcoma oncogene homolog G Chromosome: 17; Location: 17q25.3 Annotation: Chromosome 17, NC_000017.10 (79876146 . . . 79885588, complement) MIM: 602020 | 4097 |
| NFKB1 | Official Symbol NFKB1 and Name: nuclear factor of kappa light polypeptide gene enhancer in B-cells 1 [Homo sapiens] Other Aliases: DKFZp686C01211, EBP-1, KBF1, MGC54151, NF-kappa-B, NF-kappaB, NFKB-p105, NFKB-p50, p105, p50 Other Designations: DNA binding factor KBF1; NF-kappabeta; | 4790 |

TABLE 1B-continued

A list of 12 genes whose expression level can be used to determine
a TOL phenotype in a subject having a liver transplant.

| Gene Symbol | Gene Information | Entrez Gene ID |
|---|---|---|
| | nuclear factor NF-kappa-B p50 subunit; nuclear factor kappa-B DNA binding subunit; nuclear factor kappa-B, subunit 1<br>Chromosome: 4; Location: 4q24<br>Annotation: Chromosome 4, NC_000004.11<br>(103422486 . . . 103538459)<br>MIM: 164011 | |
| PDE4DIP | Official Symbol PDE4DIP and Name: phosphodiesterase 4D interacting protein [Homo sapiens]<br>Other Aliases: CMYA2, DKFZp781J054, MGC75440, MMGL<br>Other Designations: cardiomyopathy associated 2; myomegalin<br>Chromosome: 1; Location: 1q12<br>Annotation: Chromosome 1, NC_000001.10<br>(144851427 . . . 145076079, complement)<br>MIM: 608117 | 9659 |
| PHLDA2 | Official Symbol PHLDA2 and Name: pleckstrin homology-like domain, family A, member 2 [Homo sapiens]<br>Other Aliases: BRW1C, BWR1C, HLDA2, IPL, TSSC3<br>Other Designations: imprinted in placenta and liver; p17-Beckwith-Wiedemann region 1C; pleckstrin homology-like domain family A member 2; tumor suppressing subchromosomal transferable fragment cDNA 3; tumor suppressing subtransferable candidate 3; tumor-supressing STF cDNA 3<br>Chromosome: 11; Location: 11p15.5<br>Annotation: Chromosome 11, NC_000011.9<br>(2949503 . . . 2950650, complement)<br>MIM: 602131 | 7262 |
| PTBP2 | Official Symbol PTBP2 and Name: polypyrimidine tract binding protein 2 [Homo sapiens]<br>Other Aliases: FLJ34897, PTB, PTBLP, brPTB, nPTB, nPTB5, nPTB6, nPTB7, nPTB8<br>Other Designations: PTB-like; neural polypyrimidine tract binding protein; splicing regulator<br>Chromosome: 1; Location: 1p22.1-p21.3<br>Annotation: Chromosome 1, NC_000001.10<br>(97187175 . . . 97280605)<br>MIM: 608449 | 58155 |
| SENP6 | Official Symbol SENP6 and Name: SUMO1/sentrin specific peptidase 6 [Homo sapiens]<br>Other Aliases: RP1-134M13.1, FLJ11355, FLJ11887, KIAA0389, KIAA0797, SSP1, SUSP1<br>Other Designations: 2810017C20Rik; SUMO-1-specific protease; SUMO1/sentrin specific protease 6<br>Chromosome: 6; Location: 6q13-q14.3<br>Annotation: Chromosome 6, NC_000006.11<br>(76311622 . . . 76427997)<br>MIM: 605003 | 26054 |
| UBAC2 | Official Symbol UBAC2 and Name: UBA domain containing 2 [Homo sapiens]<br>Other Aliases: RP11-178C10.1, FLJ26351, FLJ30001, FLJ30548, FLJ42413, MGC90487, PHGDHL1<br>Other Designations: RP11-178C10.1; phosphoglycerate dehydrogenase like 1<br>Chromosome: 13; Location: 13q32.3<br>Annotation: Chromosome 13, NC_000013.10<br>(99852679 . . . 100038753) | 337867 |
| ZNF420 | Official Symbol ZNF420 and Name: zinc finger protein 420 [Homo sapiens]<br>Other Aliases: APAK, FLJ32191<br>Other Designations: ATM and p53-associated KZNF protein<br>Chromosome: 19; Location: 19q13.12<br>Annotation: Chromosome 19, NC_000019.9<br>(37569382 . . . 37620662) | 147923 |

In certain embodiments, the expression profile obtained is a genomic or nucleic acid expression profile, where the amount or level of one or more nucleic acids in the sample is determined, e.g., the nucleic acid transcript of the gene of interest. In these embodiments, the sample that is assayed to generate the expression profile employed in the diagnostic methods is one that is a nucleic acid sample. The nucleic acid sample includes a plurality or population of distinct nucleic acids that includes the expression information of the phenotype determinative genes of interest of the cell or tissue being diagnosed. The nucleic acid may include RNA or DNA nucleic acids, e.g., mRNA, cRNA, cDNA etc., so long as the sample retains the expression information of the host cell or tissue from which it is obtained. The sample may be prepared in a number of different ways, as is known in the art, e.g., by mRNA isolation from a cell, where the isolated mRNA is used as is, amplified, employed to prepare cDNA, cRNA, etc., as is known in the differential expression art. The sample is typically prepared from a cell or tissue harvested from a subject to be diagnosed, e.g., via biopsy of tissue, using standard protocols, where cell types or tissues from which such nucleic acids may be generated include any tissue in which the expression pattern of the to be determined phenotype exists, including, but not limited to, peripheral blood lymphocyte cells, etc., as reviewed above.

The expression profile may be generated from the initial nucleic acid sample using any convenient protocol. While a variety of different manners of generating expression profiles are known, such as those employed in the field of differential gene expression analysis, one representative and convenient type of protocol for generating expression profiles is array-based gene expression profile generation protocols. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143, 854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions, and unbound nucleic acid is then removed.

The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

"Stringent hybridization conditions" and "stringent hybridization wash conditions" in the context of nucleic acid hybridization (e.g., as in array, Southern or Northern hybridizations) are sequence dependent, and are different under different experimental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions that set forth the conditions which determine whether a nucleic acid is specifically hybridized to a surface bound nucleic acid. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C.

A specific example of stringent assay conditions is rotating hybridization at 65° C. in a salt based hybridization buffer with a total monovalent cation concentration of 1.5 M (e.g., as described in U.S. patent application Ser. No. 09/655,482 filed on Sep. 5, 2000, the disclosure of which is herein incorporated by reference) followed by washes of 0.5×SSC and 0.1× SSC at room temperature.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

The resultant pattern of hybridized nucleic acid provides information regarding expression for each of the genes that have been probed, where the expression information is in terms of whether or not the gene is expressed and, typically, at what level, where the expression data, i.e., expression profile (e.g., in the form of a transcriptome), may be both qualitative and quantitative.

Alternatively, non-array based methods for quantitating the levels of one or more nucleic acids in a sample may be employed, including those based on amplification protocols, e.g., Polymerase Chain Reaction (PCR)-based assays, including quantitative PCR, reverse-transcription PCR (RT-PCR), real-time PCR, and the like.

Where the expression profile is a protein expression profile, any convenient protein quantitation protocol may be employed, where the levels of one or more proteins in the assayed sample are determined. Representative methods include, but are not limited to: proteomic arrays, flow cytometry, standard immunoassays (e.g., western blot, ELISA assays), Mass spectrometry, etc.

Following obtainment of the expression profile from the sample being assayed, the expression profile is compared with a reference or control profile to determine the particular graft tolerant/intolerant phenotype of the cell or tissue, and therefore host, from which the sample was obtained/derived. The terms "reference" and "control" as used herein mean a standardized pattern of gene expression or levels of expression of certain genes to be used to interpret the expression signature of a given patient and assign a graft tolerant/intolerant phenotype thereto. The reference or control profile may be a profile that is obtained from a cell/tissue known to have the desired phenotype, e.g., a graft tolerant phenotype, and therefore may be a positive reference or control profile. In addition, the reference/control profile may be from a cell/tissue known to not have the desired phenotype, e.g., a graft intolerant phenotype, and therefore be a negative reference/control profile.

In certain embodiments, the obtained expression profile is compared to a single reference/control profile to obtain information regarding the phenotype of the cell/tissue being assayed. In yet other embodiments, the obtained expression profile is compared to two or more different reference/control profiles to obtain more in depth information regarding the phenotype of the assayed cell/tissue. For example, the obtained expression profile may be compared to a positive and negative reference profile to obtain confirmed information regarding whether the cell/tissue has the phenotype of interest.

The comparison of the obtained expression profile and the one or more reference/control profiles may be performed using any convenient methodology, where a variety of methodologies are known to those of skill in the array art, e.g., by comparing digital images of the expression profiles, by comparing databases of expression data, etc. Patents describing ways of comparing expression profiles include, but are not limited to, U.S. Pat. Nos. 6,308,170 and 6,228,575, the disclosures of which are herein incorporated by reference. Methods of comparing expression profiles are also described above.

The comparison step results in information regarding how similar or dissimilar the obtained expression profile is to the control/reference profile(s), which similarity/dissimilarity information is employed to determine the phenotype of the cell/tissue being assayed. For example, similarity with a positive control indicates that the assayed cell/tissue has a graft tolerant phenotype. Likewise, similarity with a negative control indicates that the assayed cell/tissue has an intolerant phenotype.

Depending on the type and nature of the reference/control profile(s) to which the obtained expression profile is compared, the above comparison step yields a variety of different types of information regarding the cell/tissue that is assayed. As such, the above comparison step can yield a positive/negative determination of a tolerant phenotype of an assayed cell/tissue. In many embodiments, the above-obtained information about the cell/tissue being assayed is employed to diagnose a host, subject or patient with respect to that host's graft tolerance, as described above.

The subject methods further find use in pharmacogenomic applications. In these applications, a subject/host/patient is first diagnosed for the presence or absence of the graft tolerant phenotype using a protocol such as the diagnostic protocol described in the preceding section. The subject is then treated using a protocol whose suitability is determined using the results of the diagnosis step. More specifically, where the identified phenotype is tolerant, a protocol that may include a reduced level of immunosuppression (i.e., immunosuppression at a level less than that which is indicated for patients not known to be graft tolerant), or no immunosuppression, may be employed to manage/treat the subject. Alternatively, where a patient is identified as having an intolerant phenotype, full immunosuppressive protocols may be employed/continued.

In many embodiments, a host is screened for the presence of a graft tolerant phenotype following receipt of a graft or transplant. The host may be screened once or serially following transplant receipt, e.g., weekly, monthly, bimonthly, half-yearly, yearly, etc., as long as the host is on immunosuppressive therapy. In certain embodiments, monitoring of the host expression profile even after immunosuppressive therapy has been reduced or discontinued is conducted to determine whether the host has maintained the tolerogenic expression profile and may continue for the lifetime of the host.

Databases of Expression Profiles of Phenotype Determinative Genes

Also provided are databases of expression profiles of graft tolerant phenotype determinative genes. Such databases will typically comprise expression profiles of various cells/tissues having graft tolerant phenotypes, negative expression profiles, etc., where such profiles are further described below.

The expression profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a user employing a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc. Thus, the subject expression profile databases are accessible by a user, i.e., the database files are saved in a user-readable format (e.g., a computer readable format, where a user controls the computer).

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention, e.g., to and from a user. One format for an output means ranks expression profiles possessing varying degrees of similarity to a reference expression profile. Such presentation provides a skilled artisan with a ranking of similarities and identifies the degree of similarity contained in the test expression profile.

Reagents and Kits

Also provided are reagents and kits thereof for practicing one or more of the above-described methods. The subject reagents and kits thereof may vary greatly. Reagents of interest include reagents specifically designed for use in production of the above-described expression profiles of phenotype determinative genes, i.e., a gene expression evaluation element made up of one or more reagents.

One type of such reagent is an array of probe nucleic acids in which the phenotype determinative genes of interest are represented. A variety of different array formats are known in the art, with a wide variety of different probe structures, substrate compositions and attachment technologies (e.g., dot blot arrays, microarrays, etc.). Representative array structures of interest include those described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280.

In many embodiments, the arrays include probes for at least 1 of the genes listed in Table 1A or Table 1B. The number of genes from Tables 1A and/or B that are represented on the array can be 1, 2, 3, 4, 5, 6, 7, 8, 9, etc. up to and including all 21 genes in Table 1A and/or all 12 genes in Table 1B. In other words, any combination of genes in Tables 1A and B can be represented on arrays of the subject invention. The subject arrays may include only those genes that are listed in Table 1A, only those genes that are listed in Table 1B, only those genes that are listed in Tables 1A or 1B. Alternatively, the arrays may include additional genes that are not listed in either Table 1A or 1B.

Another type of reagent that is specifically tailored for generating expression profiles of phenotype determinative genes (the genes listed in Table 1A and/or 1B) is a collection of gene specific primers that is designed to selectively amplify such genes. Gene specific primers and methods for using the same are described in U.S. Pat. No. 5,994,076, the disclosure of which is herein incorporated by reference. Of particular interest are collections of gene specific primers that have primers for at least 1 of the genes listed in Table 1A or 1B, often a plurality of these genes, e.g., at least 2, 5, 10, and up to and including all 21 genes in Table 1A and/or all 12 genes in Table 1B. The subject gene specific primer collections may include only those genes that are listed in Table 1A and/or 1B, or they may include primers for additional genes that are not listed in Table 1A or 1B.

The kits of the subject invention may include the above-described arrays and/or gene specific primer collections. The kits may further include one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

The subject kits may also include a phenotype determination element, which element is, in many embodiments, a reference or control expression profile that can be employed, e.g., by a suitable computing means, to make a phenotype determination based on an "input" expression profile, e.g., that has been determined with the above described gene expression evaluation element. Representative phenotype determination elements include databases of expression profiles, e.g., reference or control profiles, as described above.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Systems

Also provided are systems for practicing one or more of the above-described methods. The subject systems may vary greatly, but typically include at least a gene expression evaluation element, e.g., one or more reagents, and a phenotype determination element.

Reagents of interest include reagents specifically designed for use in production of the above-described expression profiles of phenotype determinative genes, i.e., a gene expression evaluation element made up of one or more reagents. One type of such reagent is an array of probe nucleic acids in which the phenotype determinative genes of interest are represented. A variety of different array formats are known in the art, with a wide variety of different probe structures, substrate compositions and attachment technologies. Representative array structures of interest include those described in U.S. Pat. Nos. 5,143,854; 5,288,644; 5,324,633; 5,432,049; 5,470, 710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280.

In many embodiments, the arrays include probes for at least 1 of the genes listed in Table 1A and/or 1B. In certain embodiments, the number of genes that are from Table 1A and or 1B that are represented on the array is 1, 2, 3, 4, 5, 6, 7, 8, 9, etc., up to and including all 21 genes listed in Table 1A and/or up to and including all 12 genes listed in Table 1B. The subject arrays may include only those genes that are listed in Table 1A and/or Table 1B, or they may include additional genes that are not listed in Table 1A or 1B.

Another type of reagent that is specifically tailored for generating expression profiles of phenotype determinative genes is a collection of gene specific primers that is designed to selectively amplify such genes. Gene specific primers and methods for using the same are described in U.S. Pat. No. 5,994,076, the disclosure of which is herein incorporated by reference. Of particular interest are collections of gene specific primers that have primers for at least 1 of the genes listed in Table 1A and/or Table 1B, often a plurality of these genes, e.g., 2, 3, 4, 5, 6, 7, 8, 9, etc., up to and including all 21 genes listed in Table 1A and/or up to and including all 12 genes listed in Table 1B. The subject gene specific primer collections may include only those genes that are listed in Table 1A and/or Table 1B, or they may include primers for additional genes that are not listed in Table 1A or 1B.

The systems of the subject invention may include the above-described arrays and/or gene specific primer collections. The systems may further include one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

The systems may also include a phenotype determination element, which element is, in many embodiments, a reference or control expression profile that can be employed, e.g., by a suitable computing means, to make a phenotype determination based on an "input" expression profile, e.g., that has been determined with the above described gene expression evaluation element. Representative phenotype determination elements include databases of expression profiles, e.g., reference or control profiles, as described above.

The following examples are offered by way of illustration and not by way of limitation.

infection, cancer, and diabetes (2-4). Despite the use of these drugs, chronic rejection remains an important problem that results in gradual graft loss (4, 5).

The induction of immune tolerance can prevent the rejection of grafts without immunosuppressive drugs in a variety of preclinical studies (6-9). A successful approach applied to clinical studies combined organ transplantation with the injection of hematopoietic cells from the donor to achieve stable mixed chimerism (10-13). This approach was used in the current study of kidney transplant recipients who were given total lymphoid irradiation and anti-thymocyte globulin conditioning, and a donor cell injection containing defined doses of highly enriched CD34+ hematopoietic progenitor cells mixed with CD3+ T cells (12). This conditioning regimen has been shown to protect against GVHD in preclinical models (14-17), and in recent clinical trials of 111 patients with leukemia and lymphoma followed for up to 8 years (18-19). We used this regimen to avoid the complications of GVHD, pulmonary capillary leak syndromes, severe neutropenia (<500 cells/mm$^3$), humoral rejections, and graft loss that have been reported in previous tolerance induction trials (10, 11). The first patient in the kidney transplant cohort was the subject of a previous case report (12). In order to improve the safety of the protocol, monitoring was performed to identify immune parameters that can predict the tolerant state, and guide the withdrawal of immunosuppressive drugs.

Methods

Patients

Ten patients with end stage renal failure who were candidates for kidney transplantation, and who had donors matched for 6 HLA antigens by standard genotyping were enrolled in the study. Patients were between 23 and 61 years old, and 5 were female. Details of each patient and causes of renal failure are shown in Table 2. Donors were all siblings except for the donor of patient #6 (daughter).

TABLE 2

Patient Characteristics, Conditioning, and Donor Cell Composition

| Patients[a] | Age/Gender | ESRD Cause | Total Dose TLI (cGy) | CD34+ Cell Dose (×10$^6$/kg) | CD3− Cell Dose (×10$^6$/kg) | Serum creatinine at last obs. (mg/dL) |
|---|---|---|---|---|---|---|
| 1 (41 mo.) | 48/M | unknown | 800 | 8.0 | 1 | 1.2 |
| 2 (45 mo.) | 39/F | FSGS | 800 | 8.4 | 1 | 0.8 |
| 3 (29 mo.) | 24/M | Dysplasia | 800 | 12.5 | 1 | 1.3 |
| 4 (25 mo.) | 52/M | unknown | 1,200[b] | 4.9 | 1 | 1.3 |
| 5 (21 mo.) | 34/M | IgA | 1,200 | 12.8 | 1 | 1.1 |
| 6 (20 mo.) | 61/F | DM | 1,200 | 12.2 | 1 | 1.3 |
| 7 (16 mo.) | 23/F | SLE | 1,200 | 16.7 | 10[c] | 0.9 |
| 8 (14 mo.) | 33/M | Reflux | 1,200 | 16.7 | 1 | 0.8 |
| 9 (7 mo.) | 29/F | unknown | 1,200 | 17.5 | 1 | 1.1 |
| 10 (6 mo.) | 52/F | PKD | 1,200 | 14.0 | 1 | 0.9 |

ESRD—end stage renal disease;
FSGS—focal segmental glomerulosclerosis;
IgA—IgA nephropathy;
DM—diabetes mellitus;
SLE—Systemic lupus erythematosus;
PKD—polycystic kidney disease
[a]parentheses show duration of follow-up
[b]dose increased to facilitate persistent chimerism
[c]dose increased to achieve complete chimerism

EXPERIMENTAL

Example 1

Recipients of kidney transplants require the lifelong use of immunosuppressive drugs to prevent graft rejection (1, 2). The use of these drugs is associated with a variety of cumulative side effects including increased risks of heart disease, Conditioning TLI was administered as 10 doses of 80 or 120 cGy each to the supradiaphragmatic lymph nodes, thymus, subdiaphragmatic lymph nodes, and spleen during the first 11 days post-transplant as described previously (12, 13). Rabbit anti-thymocyte globulin (Thymoglobulin, Genzyme) was given intravenously (1.5 mg per kilogram for each of 5 daily doses) starting with an intraoperative injection. Patients received prophylactic medications against fungal, bacterial, and viral infections. The protocol was approved by the institutional review board of Stanford University, and all recipients and donors provided written informed consent.

Donor Cells

Donors received a 5 day course of granulocyte colony stimulating factor at a dose of 16 mg per kilogram per day, and mononuclear cells were harvested by 1 apheresis in the first 4 patients and by 2 aphereses in the last 6 patients to increase the dose of hematopoietic progenitor cells (Table 2). CD34+ cells were enriched with the use of an Isolex column (Baxter), and cryopreserved until infusion into recipients. Column flow through cells were added back to CD34+ cells to achieve a defined dose of CD3+ T cells in the infusion as shown in Table 2.

Measurement of Chimerism

Serial chimerism measurements were performed using DNA from blood mononuclear cells enriched for T cells, B cells, natural killer cells, and granulocytes on immunomagnetic beads (Dyna-beads, Dynal) coated with monoclonal antibodies to CD3, CD19, CD56, and CD15 respectively. The percentage of donor type cells was determined by analysis of polymorphisms in the lengths of short tandem repeats (STR) (12, 20).

Immunofluorescent Staining and Analysis of T Cell Subsets

Blood mononuclear cells were stained with fluorochrome conjugated monoclonal antibodies against CD3, CD4, CD8, CD62L, CD45RA CD45RO, CD25 (BD Pharmingen), and Vα24 and Vβ11 (Beckman Coulter) (21). Multi-color flow cytometry was used to identify T cell subsets with the use of standard techniques and equipment (LSR and FACS Vantage cytometers, BD Biosciences) (21). CD4+CD25+ Treg cells were analyzed for the intracellular staining of FoxP3 with an eBiosciences kit.

Gene Microarray Analysis

Recipient blood mononuclear cells were analyzed using gene microarrays to identify a "tolerant" gene expression pattern using modifications of methods described previously (22).

T Cell Responses to Antigens

Immune response assays were performed by culturing recipient blood mononuclear cells with recall antigens, third party mononuclear cells, or donor dendritic cells and measuring 3H-thymidine incorporation as described previously (12, 13, 23, 24).

Results

Transplantation Protocol and Assessment of Safety

Ten patients were conditioned with total lymphoid irradiation and rabbit antithymocyte globulin after kidney transplantation. Hospitalization for transplantation surgery was between 4 to 7 days (median 5 days). Donor CD34+ selected cells and a defined dose of T cells were injected intravenously on day 11 in the outpatient clinic (Table 2). One patient with active systemic lupus received a T cell dose of $10 \times 10^6$/kg in order to induce complete chimerism to treat lupus. All patients were given mycophenolate mofetil for 1 month (2 grams per day) after the donor cell infusion, and therapeutic doses (800-1200 ng per milliliter peak blood level) of cyclosporine for 3 months starting on day 0. Cyclosporine was tapered starting at 3 months and discontinued after at least 6 months if patients met immunosuppressive drug withdrawal criteria that included (1) persistent chimerism for at least 6 months, (2) no evidence of GVHD, and (3) no rejection episodes. The rapidity of complete withdrawal varied from shortly after 6 months to 17 months depending on whether chimerism was stable or declining and on recurrence of the original disease.

The nadir white blood cell counts were above $1 \times 10^3$ per microliter in 9 of 10 patients, and the median was $1.3 \times 10^3$ per microliter. None of the patients developed acute or chronic GVHD, pulmonary capillary leak syndromes or early humoral rejections. Three had return hospitalizations for neutropenic fever, ureteral stricture, and acute cellular rejection. Infection was diagnosed in 1 patient with cytomegalovirus (fever and malaise), and 2 with varicella zoster, and treatment was given without hospitalization. Patient #1, who had a history of coronary artery disease, died suddenly 41 months after transplantation during a bicycle tour in Europe. All other patients are alive and well.

Serial Monitoring of Graft Function, Chimerism, and T Cell Subsets in Patients Who Stopped Anti-Rejection Medications Of the 10 patients enrolled, 5 who were followed for more than 12 months had immunosuppressive drugs discontinued after meeting drug withdrawal criteria. FIG. 1 (top panels) shows the serial serum creatinine measurements of the latter patients. There was a rapid decrease in creatinine concentrations shortly after transplantation, and concentrations remained stable between 0.8 to 1.4 mg per deciliter after stopping anti-rejection drugs. The drugs have been discontinued for 35, 14, 8, 7, and 6 months without evidence of graft dysfunction as judged by creatinine clearance, urinary protein, and surveillance biopsies.

FIG. 1 also shows the serial measurements of the percentages of donor type cells among blood T cells, B cells, NK cells, and granulocytes. In patients, #1 and 7, there was a pattern of stable mixed chimerism. Patients #4 and 5 showed a declining pattern of mixed chimerism, and donor type cells could no longer be detected at 400 to 500 days after transplant. Patient #7, who received a high dose of donor T cells, developed complete chimerism by 3 months.

The two bottom panels of FIG. 1 show serial changes in T cell subsets in the blood after transplantation including naïve (CD62L+CD45RA+RO−) CD4+, naïve CD8+ T cells, and CD4+CD25+ Treg cells. Naïve T cells mediate, and Treg and NKT cells suppress alloimmunity (8, 9, 25-31). FIG. 1 shows that all 5 patients had a marked (about 100 fold) reduction of the absolute number of all T cells subsets shortly after conditioning and donor cell injection, and a recovery of these numbers close to pretransplant levels in the first several months after transplantation. The fall in naïve T cells was more severe than that of the Treg cells, such that the ratio of the Treg/CD4 naïve T cells rose from about 0.1 to more than 2 in all 5 patients at the first posttransplant time point, and the high ratios persisted for more than 1 year in 4 patients. The absolute number of naïve CD8+ T cells returned to pretreatment levels more rapidly than the naïve CD4+ T cells. A similar pattern was observed with total CD8+ and CD4+ T cells. The absolute numbers of NKT cells (Valpha24+ Vbeta11+) and the ratios of NKT cells to naïve total T cells were measured serially also. Although NKT cells suppress rejection and GVHD in preclinical models (17, 27, 28, 31), the NKT/naïve total T cell ratios did not increase uniformly or persistently.

Figure 2:
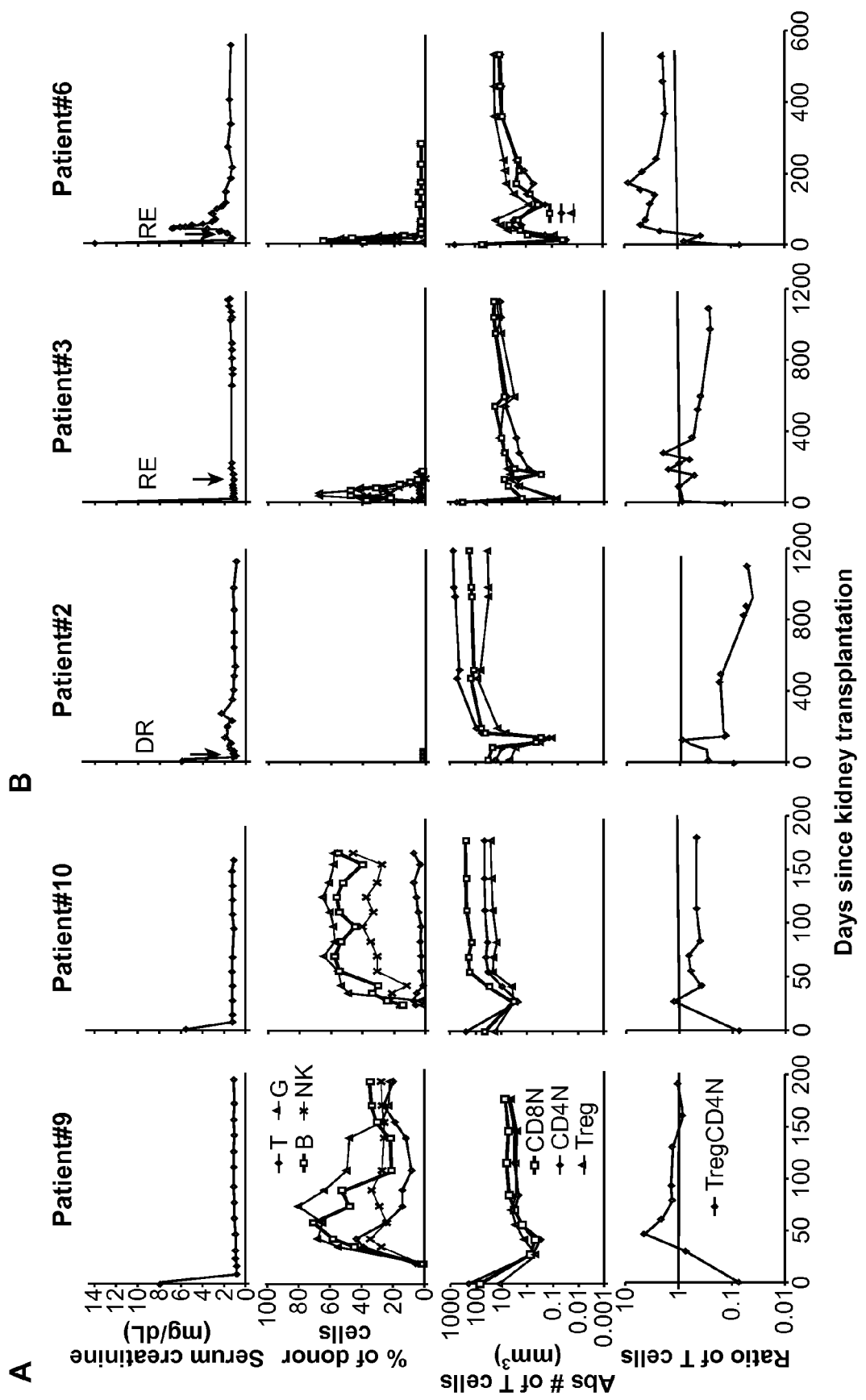
FIG. 2. Graft function, chimerism, and T cell subsets in patients in the midst of immunosuppressive drug withdrawal and in those who did not meet criteria for withdrawal of immunosuppressive drugs. A, top panels show serial creatinine measurements of patients #9 and 10 who met drug withdrawal criteria and are in the midst of withdrawal. B, top panels show serial creatinine concentrations of patients who did not meet withdrawal criteria, and arrows show time points of FSGS disease recurrence (DR) in patient #2, and of rejection episodes (RE) confirmed by biopsy in patients #3, and 6. Chimerism and T cell subset measurements are shown also.

FIG. 2A shows that patients #9 and 10, who have been followed for 7 and 6 months respectively, met immunosuppressive drug withdrawal criteria, and are stable mixed chimeras without rejection episodes or GVHD. Both have stable creatinine levels below 1.2 mg/dL. In summary, 7 of 10 patients met drug withdrawal criteria, 5 were withdrawn and 2 are in the midst of withdrawal.

Serial Monitoring of Graft Function, Chimerism, and T Cell Subsets in Patients Who Failed to Meet Criteria for Withdrawal of Anti-Rejection Drugs FIG. 2B (top panels) shows the serial creatinine concentrations of 3 patients who failed to meet drug withdrawal criteria. Patient #2 had a biopsy confirmed recurrence of her underlying disease, focal segmental glomerulosclerosis (FSGS), in the transplanted kidney. She was treated with plasmapheresis, and chimerism never developed. Patients #3 and #6 developed chimerism in the first month transplant. Patient #3 developed a mild cellular rejection episode (Banff IB) and loss of chimerism during tapering of cyclosporine in month 6 (FIG. 2B). Patient #6 developed a cellular rejection episode (Banff IIA) during the second month, and lost chimerism shortly thereafter. Both were treated with intensified anti-rejection medications, and the serum creatinine levels returned to the pre-rejection values that continue to the present. Maintenance therapy includes cyclosporine and mycophenolate mofetil (patient #2), cyclosporine alone (#3), and tacrolimus, mycophenolate mofetil, and prednisone (#6). FIG. 2B (bottom 2 panels) shows the serial changes in the T cell subsets. The ratios of Tregs/CD4+ naïve T cells were all below 1 at the first posttransplant observations.

Specific Unresponsiveness to Donor Alloantigens in Patients Off Drugs

The immune responses to third party and donor alloantigens and to microbial recall antigens were determined during the second year in 3 of 5 patients who discontinued immunosuppressive drugs. In these 3 patients, posttransplant responses to donor alloantigens were significantly reduced as compared to the pretransplant values, and posttransplant responses to third party alloantigens and microbial antigens were not significantly reduced. Two of 3 patients who were maintained on immunosuppressive drugs were also tested during the second year. In contrast to patients off drugs, their pre and posttransplant responses to donor alloantigens were not significantly different.

Monitoring Changes in Gene Microarray Patterns

Since previous microarray cross sectional studies identified a "tolerant" gene expression pattern that distinguished "operationally tolerant" patients from those maintained on conventional immunosuppressive drugs and from healthy donors (22), we monitored the pre and posttransplant gene array patterns from patients enrolled in the tolerance induction study.

Figure 5:
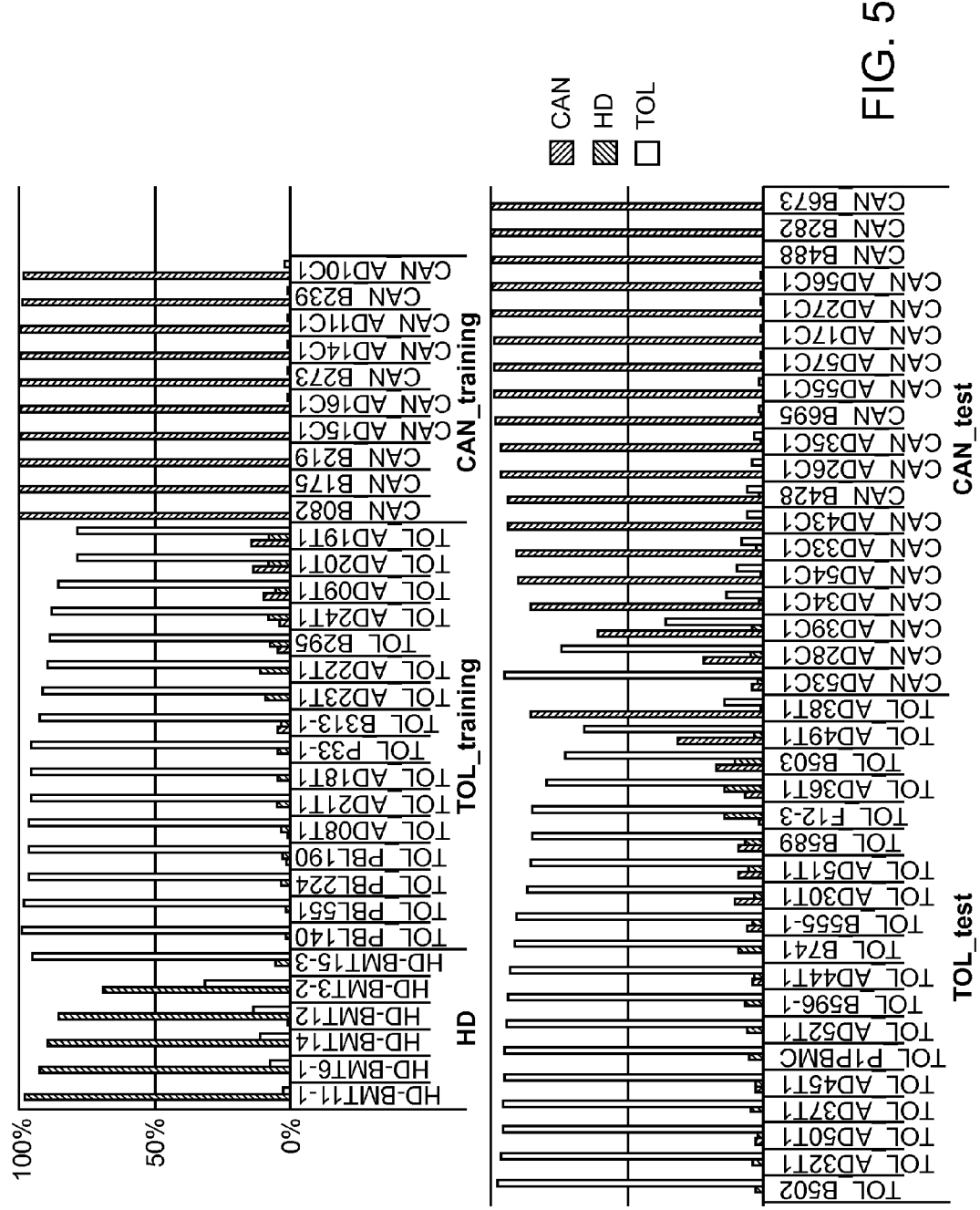
FIG. 5 shows tolerance prediction scores using the 21 gene biomarker set for groups of patients and controls, with 100% representing the closest match. Agilent microarray analysis on 70 PBL samples were performed and analyzed. Samples included 35 operationally tolerant (TOL), 29 chronic rejection (or chronic allograft nephropathy; CAN), and 6 healthy donors (HD). The training samples (top panel; 6 HD, 10 CAN and 16 TOL) and test samples (bottom panel; 19 CAN and 19 TOL) are indicated. As shown in the bottom panel of FIG. 5, only two mis-classifications occurred in the 19 sample CAN test set (CAN_test; 89% sensitivity) while only 1 mis-classification occurred in the 19 sample TOL test set (TOL-test; 95% sensitivity).

A new set of 21 unique genes was initially validated to discriminate between recipients with "operational tolerance" (TOL) versus those with chronic (CAN) or no rejection on immunosuppressive drugs, and healthy donors (HD). FIG. 5 shows tolerance prediction scores using the 21 gene biomarker set for groups of patients and controls, with 100% representing the closest match. For FIG. 5, Agilent microarray analysis on 70 PBL samples were performed and analyzed. Samples included 35 operationally tolerant (TOL), 29 chronic rejection (or chronic allograft nephropathy; CAN), and 6 healthy donors (HD). The training samples (top panel; 6 HD, 10 CAN and 16 TOL) and test samples (bottom panel; 19 CAN and 19 TOL) are indicated. As shown in the bottom panel of FIG. 5, only two mis-classifications occurred in the 19 sample CAN test set (CAN_test; 89% sensitivity) while only 1 mis-classification occurred in the 19 sample TOL test set (TOL-test; 95% sensitivity).

Table 3 provides data showing the expression level changes of the 21 gene biomarker panel in TOL versus CAN training samples. Data is from exemplary Agilent microarray probes specific for one of the 21 biomarker genes. Agilent probe ID numbers are shown in the left column with the gene name of the intended target in the following column (note that two probes detect IGH@). CAN and TOL scores, their ratios and the fold changes in expression are shown in the following columns. Genes with positive fold change are upregulated in TOL vs. CAN samples whereas genes with negative fold change are downregulated in TOL vs. CAN samples.

TABLE 3

Expression data for 21 biomarker genes for kidney allograft tolerance.

| Probe ID | Name | CAN score | TOL score | Ratio | Fold* |
|---|---|---|---|---|---|
| A_23_P167168 | IGJ | −0.2745 | 0.1715 | 3.453913165 | 3.453913165 |
| A_23_P37736 | TNFRSF17 | −0.2145 | 0.1341 | 3.201508892 | 3.201508892 |
| A_32_P200144 | IGH@ | −0.2061 | 0.1288 | 3.205147016 | 3.205147016 |
| A_32_P47643 | FAM110C | −0.1477 | 0.0923 | 2.24651885 | 2.24651885 |
| A_24_P24371 | IGHG4 | −0.1403 | 0.0877 | 2.766827498 | 2.766827498 |
| A_24_P169873 | IGHA2 | −0.1224 | 0.0765 | 2.118149336 | 2.118149336 |
| A_23_P158817 | IGH@ | −0.1003 | 0.0627 | 2.462754139 | 2.462754139 |
| A_32_P96719 | SHCBP1 | −0.0867 | 0.0542 | 1.793550389 | 1.793550389 |
| A_24_P20469C | PRAMEF3 | 0.0786 | −0.0491 | 0.373452048 | −2.677719949 |
| A_23_P153571 | IGFL2 | 0.0696 | −0.0435 | 0.244359792 | −4.092326293 |
| A_32_P133916 | BNC2 | −0.0695 | 0.0434 | 2.090806778 | 2.090806778 |
| A_23_P209625 | CYP1B1 | −0.0559 | 0.0349 | 1.608468621 | 1.608468621 |
| A_23_P125977 | C1QC | 0.0505 | −0.0315 | 0.403376789 | −2.479071746 |
| A_23_P10518 | TFDP3 | 0.0494 | −0.0309 | 0.542111309 | −1.84463962 |
| A_23_P208880 | UHRF1 | −0.0364 | 0.0228 | 1.776832215 | 1.776832215 |
| A_23_P402279 | VN1R2 | −0.0192 | 0.012 | 1.542618515 | 1.542618515 |
| A_23_P171336 | NXF3 | 0.0157 | −0.0098 | 0.56763107 | −1.761707653 |
| A_24_P933448 | RLBP1L1 | −0.0119 | 0.0074 | 1.523505215 | 1.523505215 |
| A_23_P207564 | CCL4 | −0.0104 | 0.0065 | 1.780351103 | 1.780351103 |
| A_23_P250747 | GDEP | 0.0097 | −0.006 | 0.607590273 | −1.645845966 |
| A_23_P51085 | SPC25 | −0.0082 | 0.0051 | 1.734334314 | 1.734334314 |
| A_24_P932981 | KLF6 | −0.0033 | 0.0021 | 2.008160926 | 2.008160926 |

*Genes with positive "fold" change are upregulated in TOL vs. CAN; genes with negative "fold" change are downregulated in TOL vs. CAN.

Figure 3:
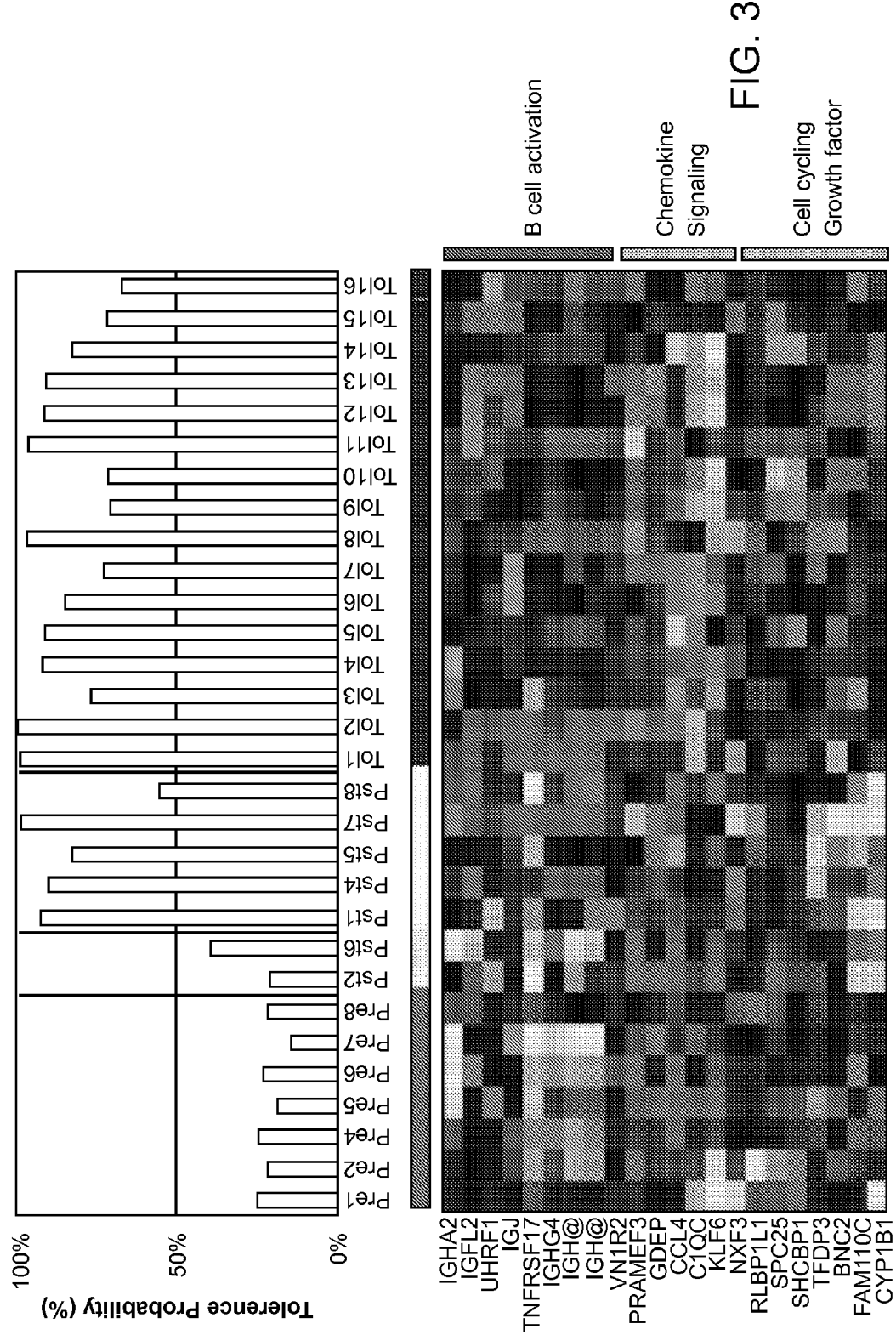
FIG. 3. Heat map of gene microarrays and tolerance prediction scores of blood samples from protocol patients and from operationally tolerant patients. Heat map shows patterns of expression of 21 unique genes that discriminated operationally tolerant (TOL) from non-tolerant individuals (e.g., chronic rejection (chronic allograft nephropathy; CAN), healthy donors/controls (HD), etc.). Pre (Pre) and posttransplant (Pst) blood samples available from patients #1, 2, 4, 5, 6, 7, and 8 were compared to those from operationally tolerant patients (Tol 1-16). Pretransplant samples are grouped by a horizontal red bar (Pre), posttransplant samples are grouped by a yellow bar from patients who did not meet drug withdrawal criteria (Pst), by a blue bar from patients who stopped immunosuppressive drugs (Pst), and a black bar from operationally tolerant patients. Bar graph above heat map shows tolerance prediction scores as determined by matching with the tolerance signature from a group of "operationally" tolerant patients as judged by Probability Analysis of Microarrays. Posttransplant samples are the first samples monitored. There were 22 probes used for the 21 unique genes (two probes for IGH@ were used). Gene identifiers are shown on left side of map, and gene groupings are shown on right.

FIG. 3 shows a heat map of the expression pattern of the 21 genes using posttransplant blood samples from 16 "operationally tolerant" patients, first posttransplant samples from 5 patients who were withdrawn from immunosuppressive drugs in the current study, first posttransplant samples in 2 patients maintained on drugs in the current study, and 7 available pretransplant samples. The bar graph above the heat map shows that the tolerance prediction scores determined by Predictive Analysis of Microarray testing (32) were well below 50% in all pretransplant samples, and in the first posttransplant samples of study patients maintained on drugs. In contrast, the prediction scores from first posttransplant samples from all study patients off drugs and from all "operationally tolerant" patients were between 55% and 100% (FIG. 3).

With the objective of further refining the gene set into a manageable number of genes for PCR-based analyses, the array data was analyzed by logistic regression. In this analysis, a three gene model for kidney tolerant phenotype was identified, where the three genes are FAM110C, IGHG4 and KLF6. The equation is as follows:

$$\theta = \frac{e^{[-4.4116+(6.828*FAM110C)+(158.3*IGHG4)+(6.3819*KLF6)]}}{1 + e^{[-4.4116+(6.828*FAM110C)+(158.3*IGHG4)+(6.3819*KLF6)]}}$$

where gene names indicate the fold-change data measurements at each locus.

Figure 4:
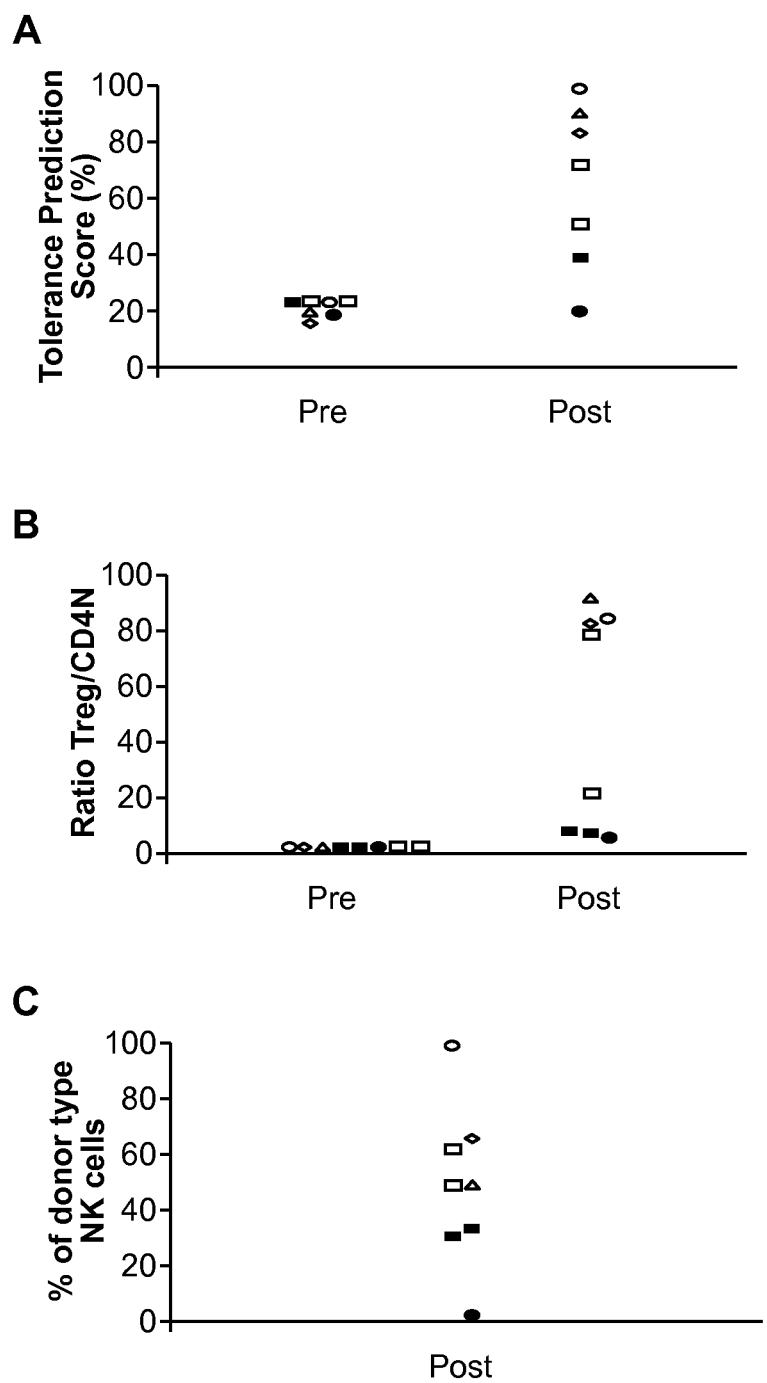
FIG. 4. Immune monitoring parameters that distinguish patients followed for more than 1 year who are on or off immunosuppressive drugs. A, shows the pre and first posttransplant gene array tolerance prediction scores. The open symbols represent patients who are off drugs, and the closed symbols represent patients who are on drugs. B, shows the pre and first posttransplant ratios of Treg/CD4+ naïve T cells. C, shows the maximum percentages of donor type cells among NK cells in protocol patients within the first 50 days after transplantation. Pre and posttransplant samples from 8 patients were available for B and C, and from 7 patients for A. Samples in A were obtained from 1 to 5 months posttransplant, and samples in B and C within the first 30 or 50 days respectively. Patients are grouped by different chimerism patterns as follows: ●—primary engraftment failure (patient #2); ■—loss of chimerism with rejection episodes during drug reductions (patients #3 and 6); ○—complete chimerism (patient #7); □—stable mixed chimerism (patients #1 and 8); ▲—loss of chimerism before stopping drugs (patient #4); ◇—loss of chimerism after stopping drugs (patient #5).`

Early Monitoring Parameters that Distinguish Patients on or Off Drugs after 12 Months We analyzed the immune monitoring data of the 8 patients who were followed for more than 12 months. Pre and first posttransplant tolerance prediction scores, ratios of Treg/CD4+ naïve T cells, and the maximum levels of chimerism among NK cells by day 50 were compared using thresholds that have been reported to be predictive of tolerance (22), immune suppression (8, 9, 27), or stability of chimerism (20) in previous studies. FIG. 4A shows that all 5 patients who stopped drugs had tolerance prediction scores above 50%, whereas pre transplant scores of all patients and posttransplant scores of patients on maintenance drugs were below 50%. Posttransplant values of patients on and off drugs were statistically significantly different (p<0.04) using the Fisher exact test. All 5 patients off drugs had posttransplant Treg/CD4+ naïve ratios that were more than 1, whereas pretransplant ratios of all patients and posttransplant ratios of patients on drugs were below 1 (FIG. 4B). Differences in posttransplant values between the 2 groups were significant (p<0.02). The maximum levels of donor type cells among NK cells by day 50 were above 35% for all 5 patients on drugs, and were below 35% for patients off drugs (p<0.02) (FIG. 4C).

DISCUSSION

The goal of the current study was to achieve persistent mixed chimerism, tolerance, and complete immunosuppressive drug withdrawal safely in HLA matched kidney and hematopoietic cell transplant recipients conditioned with total lymphoid irradiation and antithymocyte globulin. At the last observation point all patients had excellent graft function. Seven of 10 patients developed persistent chimerism for at least 6 months, and 5 of these followed for at least 12 months were withdrawn from all immunosuppressive drugs for 6 to 35 months. Patients from this group had specific unresponsiveness to donor alloantigens in the mixed leukocyte reaction. There were 3 patients without persistent chimerism who were maintained on immunosuppressive drugs after rejection episodes or return of underlying disease (FSGS), and who responded to donor alloantigens. The results show that complete withdrawal of drugs without subsequent rejection episodes was accomplished after at least 6 months of persistent chimerism. The intentional establishment of persistent mixed chimerism in a series of HLA matched or mismatched patients has not been reported previously. Immune monitoring showed that patients withdrawn from immunosuppressive drugs had significantly higher ratios of Treg/naïve CD4+ T cells, gene array tolerance prediction scores, and chimerism among NK cells at early time points after transplantation as compared to the patients who were maintained on drugs. These monitoring tests can help guide the rapidity of withdrawal of immunosuppressive drugs, and results suggest that drug tapering be delayed until 6 months in patients with low test scores. We are applying this strategy to the last 2 patients.

Although the persistence of chimerism for more than 6 months was associated with the development of tolerance, chimerism per se was not necessary or sufficient to ensure tolerance. Some patients with chimerism had rejection episodes within the first 6 months during drug reduction. Permanent chimerism is not necessary to maintain tolerance, since some patients who lost chimerism after 1 year had continued good graft function without immunosuppressive drugs and had specific unresponsiveness to donor antigens. Previous clinical studies showed that tolerance can be induced without chimerism, but graft loss in non-tolerant study patients and a high incidence of rejection episodes were observed (11, 33, 34).

In conclusion, persistent chimerism and tolerance to HLA matched kidney transplants can be achieved safely. Immune monitoring of Treg/naïve CD4+ T cell ratios, levels of early chimerism among NK cells, and gene array testing may provide assistance in guiding the withdrawal of immunosuppressive drugs.

REFERENCES

1. Srinivas T R, Schold J D, Guerra G, Eagan A, Bucci C M, Meier-Kriesche H U. Mycophenolate mofetil/sirolimus compared to other common immunosuppressive regimens in kidney transplantation. Am J Transplant 2007; 7:586-94.
2. Srinivas T R, Meier-Kriesche H U. Minimizing immunosuppression, an alternative approach to reducing side effects: objectives and interim result. Clin J Am Soc Nephrol 2008; 3 Suppl 2:S101-16.
3. Cosio F G, Kudva Y, van der Velde M, et al. New onset hyperglycemia and diabetes are associated with increased cardiovascular risk after kidney transplantation. Kidney Int 2005; 67:2415-21.
4. Yang H. Maintenance immunosuppression regimens: conversion, minimization, withdrawal, and avoidance. Am J Kidney Dis 2006; 47:537-51.
5. Tantravahi J, Womer K L, Kaplan B. Why hasn't eliminating acute rejection improved graft survival? Annu Rev Med 2007; 58:369-85.
6. Field E H, Strober, S. Tolerance, mixed chimerism and protection against GVHD after TLI. Philos Trans R Soc Lond B Biol Sci 2001; 356:1-10.
7. Sykes M. Mixed chimerism and transplant tolerance. Immunity 2001; 14:417-24.
8. Wood K J, Sakaguchi S. Regulatory T cells in transplantation tolerance. Nat Rev Immunol 2003; 3:199-210.
9. Kang S M, Tang Q, Bluestone J A. CD4+CD25+ regulatory T cells in transplantation: progress, challenges and prospects. Am J Transplant 2007; 7:1457-63.
10. Fudaba Y, Spitzer T R, Shaffer J, et al. Myeloma responses and tolerance following combined kidney and nonmyeloablative marrow transplantation: in vivo and in vitro analyses. Am J Transplant 2006; 6:2121-33.
11. Kawai T, Cosimi A B Spitzer T R, et al. HLA-mismatched renal transplantation without maintenance immunosuppression. N Engl J Med 2008; 358:353-61.

12. Scandling J D, Busque S, Dejbakhsh-Jones S, et al. Tolerance and chimerism after renal and hematopoietic-cell transplantation. N Engl J Med 2008; 358:362-8.
13. Millan M T, Shizuru J A, Hoffmann P, et al. Mixed chimerism and immunosuppressive drug withdrawal after HLA-mismatched kidney and hematopoietic progenitor transplantation. Transplantation 2002; 73:1386-91.
14. Slavin S, Strober S, Fuks Z, Kaplan H S. Long-term survival of skin allografts in mice treated with fractionated total lymphoid irradiation. Science 1976; 193:1252-4.
15. Slavin S, Strober S, Fuks Z, Kaplan H S. Induction of specific tissue transplantation tolerance using fractionated total lymphoid irradiation in adult mice: long-term survival of allogeneic bone marrow and skin grafts. J Exp Med 1977; 146:34-48.
16. Lan F, Zeng D, Higuchi M, Huie P, Higgins J P, Strober S. Predominance of NK1.1+TCR alpha beta+ or DX5+TCR alpha beta+ T cells in mice conditioned with fractionated lymphoid irradiation protects against graft-versus-host disease: "natural suppressor" cells. J Immunol 2001; 167:2087-96.
17. Pillai A B, George T I, Dutt S, Strober S. Host natural killer T cells induce an interleukin-4-dependent expansion of donor CD4+CD25+Foxp3+ T regulatory cells that protects against graft-versus-host disease. Blood 2009; 113:4458-67.
18. Lowsky R, Takahashi T, Liu Y P, et al. Protective conditioning for acute graft-versus-host disease. N Engl J Med 2005; 353:1321-31.
19. Kohrt H E, Turnbull B B, Heydari K, et al. TLI and ATG conditioning with low risk of graft-versus-host disease retains anti-tumor reactions after allogeneic hematopoietic cell transplantation from related and unrelated donors. PMID 19423725 Blood 2009.
20. Baron F, Baker J E, Storb R, et al. Kinetics of engraftment in patients with hematologic malignancies given allogeneic hematopoietic cell transplantation after nonmyeloablative conditioning. Blood 2004; 104:2254-62.
21. Takahashi T, Dejbakhsh-Jones S, Strober S. Expression of CD161 (NKR-P1A) defines subsets of human CD4 and CD8 T cells with different functional activities. J Immunol 2006; 176:211-6.
22. Brouard S, Mansfield E, Braud C, et al. Identification of a peripheral blood transcriptional biomarker panel associated with operational renal allograft tolerance. Proc Natl Acad Sci USA 2007; 104:15448-53.
23. Mehta-Damani A, Markowicz S, Engleman E G. Generation of antigen-specific CD8+ CTLs from naive precursors. J Immunol 1994; 153:996-1003.
24. Zhang A L, Colmenero P, Purath U, et al. Natural killer cells trigger differentiation of monocytes into dendritic cells. Blood 2007; 110:2484-93.
25. Hoffmann P, Ermann J, Edinger M, Fathman C G, Strober S. Donor-type CD4(+)CD25(+) regulatory T cells suppress lethal acute graft-versus-host disease after allogeneic bone marrow transplantation. J Exp Med 2002; 196:389-99.
26. Higuchi M, Zeng D, Shizuru J, et al. Immune tolerance to combined organ and bone marrow transplants after fractionated lymphoid irradiation involves regulatory NK T cells and clonal deletion. J Immunol 2002; 169:5564-70.
27. Zeng D, Lewis D, Dejbakhsh-Jones S, et al. Bone marrow NK1.1(−) and NK1.1(+) T cells reciprocally regulate acute graft versus host disease. J Exp Med 1999; 189:1073-81.
28. Joffre O, Santolaria T, Calise D, et al. Prevention of acute and chronic allograft rejection with CD4+CD25+Foxp3+ regulatory T lymphocytes. Nat Med 2008; 14:88-92.
29. Dutt S, Tseng D, Ermann J, et al. Naive and memory T cells induce different types of graft-versus-host disease. J Immunol 2007; 179:6547-54.
30. Anderson B E, McNiff J, Yan J, et al. Memory CD4+ T cells do not induce graft-versus-host disease. J Clin Invest 2003; 112:101-8.
31. Seino K I, Fukao K, Muramoto K, et al. Requirement for natural killer T (NKT) cells in the induction of allograft tolerance. Proc Natl Acad Sci USA 2001; 98:2577-81.
32. Tibshirani R, Hastie T, Narasimhan B, Chu G. Diagnosis of multiple cancer types by shrunken centroids of gene expression. Proc Natl Acad Sci USA 2002; 99:6567-72.
33. Strober S, Dhillon M, Schubert M, et al. Acquired immune tolerance to cadaveric renal allografts. A study of three patients treated with total lymphoid irradiation. N Engl J Med 1989; 321:28-33.
34. Saper V, Chow D, Engleman E D, et al. Clinical and immunological studies of cadaveric renal transplant recipients given total-lymphoid irradiation and maintained on low-dose prednisone. Transplantation 1988; 45:540-6.

Example 2

In this Example, gene expression biomarkers for determining a graft tolerant phenotype (TOL) in subjects having a liver transplant are identified.

Methods 46 unique whole blood samples from 4 demographically matched patient phenotypes were run on Agilent Whole Human Genome 44K microarrays. Patients included: 7 operational tolerant pediatric liver transplant patients who were on no medications for between 9.3 to 17.1 years (P-TOL); 13 patients with biopsy proven acute rejection (AR); 7 patients on low-dose prograf monotherapy/minimal immunosuppression (MIS); and 13 stable patients on dual immunosuppression. Additionally, samples from 6 healthy donors (HD) were also analyzed. Standardized bioinformatic analyses were applied and significant TOL genes were mapped by AILUN to published data on Affymetrix arrays from an operational tolerance study in adult liver transplant recipients (A-TOL; Llordella et al "Multiparameter immune profiling of operational tolerance in liver transplantation" Am J. Transplant. 2007 February; 7(2):309-19).

Results

Twelve unique genes were identified (FDR<5%) by prediction analysis of microarrays (PAM) as a minimum gene set to cross-validate and predict P-TOL with 100% sensitivity and 85% specificity (see Table 1B and Table 4). These genes are enriched in liver regeneration and 11/12 genes are regulated by NFkB1 and SMAD3. The tolerant specific genes are highly expressed in T cells, CD34+ endothelial and NK cells. 65% MIS and STA patients were predicted as TOL based on prediction probability scores >50%. These genes also correctly predicted 76% of the 17 A-TOL samples and 95% of the 21 non-TOL samples in the adult study. The most significant 100 genes from the adult tolerance (A-TOL) published study (Llordella et al, cited above) could not back predict any of the P-TOL samples in the tolerance class. There is no association between gene expression and age either at the sample time or age at the transplant for the 12 gene set.

TABLE 4

Expression data for 12 biomarker genes for liver allograft tolerance.

| ID | Name | Non TOL score* | TOL score* | GeneID | Cell Type |
|---|---|---|---|---|---|
| 213341_at | FEM1C | 0.154 | −0.1902 | 56929 | E, B, D, T, NK |
| 1554614_a_at | PTBP2 | 0.0776 | −0.0959 | 58155 | E, T |
| 209160_at | AKR1C3 | −0.0693 | 0.0856 | 8644 | E, NK |
| 239876_at | NFKB1 | 0.045 | −0.0556 | 4790 | E, B, D, T, NK |
| 216836_s_at | ERBB2 | −0.0407 | 0.0503 | 2064 | E, B, T, NK |
| 209803_s_at | PHLDA2 | 0.0222 | −0.0274 | 7262 | E, B, D, T, NK |
| 242761_s_at | ZNF420 | −0.0172 | 0.0213 | 147923 | T |
| 244511_at | PDE4DIP | −0.0165 | 0.0203 | 9659 | E, B, D, T, NK |
| 210896_s_at | ASPH | 0.0057 | −0.007 | 444 | D, E |
| 239200_at | UBAC2 | 0.0041 | −0.0051 | 337867 | E, D, T, NK |
| 204970_s_at | MAFG | 0.004 | −0.0049 | 4097 | E, B, D, NK |
| 240016_at | SENP6 | −0.0013 | 0.0016 | 26054 | E, B, D, T, NK |

E = endothelial cell, B = B cell, D = dendritic cell, T = T cell, NK = Natural Killer Cell
*Genes with positive change from Non TOL score to TOL score are upregulated in TOL phenotype (in bold); genes with negative change from Non TOL score to TOL score are downregulated in TOL phenotype.

CONCLUSION

Specific peripheral transcriptional programs can be identified in operational tolerance in pediatric recipients of liver allografts (P-TOL), distinct from those previously identified in adult operationally tolerant liver recipients (A-TOL). This findings provides a means to non-invasively monitor patients for graft tolerance in a serial manner, providing a basis for immunosuppression minimization. While not being bound by theory, it is noted that the 12 biomarker genes identified in this study are highly expressed in specific peripheral blood lymphocyte subsets, and thus their coordinated regulation (e.g., by specific cytokines) may support the maintenance of operational tolerance in children following liver transplantation.

As detailed above, biomarkers for monitoring induced tolerance in adult renal and liver transplant patients are provided herein. Gene expression signatures characteristic of graft tolerance can be detected in whole blood lysates obviating the need for more invasive methods of sampling (e.g., from graft biopsy tissue).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of determining whether a subject who has received renal allograft has a graft tolerant or a graft intolerant phenotype comprising:
   (a) evaluating the level of expression of at least three genes in a sample from a subject who has received a renal allograft to obtain a gene expression result, wherein said at least three genes are selected from the group consisting of: BNC2, C1QC, CCL4, CYP1B1, FAM110C, GDEP, IGFL2, IGH@, IGHA2, IGHG4, IGJ, KLF6, NXF3, PRAMEF3, RLBP1L1, SHCBP1, SPC25, TFDP3, TNFRSF17, UHRF1 and VN1R2, wherein said evaluating comprises:
   contacting said sample with a collection of reagents for assaying for an expression product of each of said at least three genes; and
   assessing, using said collection of reagents, the amount of each of said expression products in said sample;
   (b) comparing said gene expression result to at least one reference gene expression profile, wherein said reference gene expression profile is selected from: a graft tolerant phenotype gene expression profile and a graft intolerant phenotype gene expression profile; and
   (c) determining that said subject has a graft tolerant phenotype based on said comparing when said gene expression result is similar to said graft tolerant phenotype gene expression profile and/or is dissimilar to said graft intolerant phenotype gene expression profile; or determining that said subject has a graft intolerant phenotype based on said comparing when said gene expression result is dissimilar to said graft tolerant phenotype gene expression profile and/or is similar to said graft intolerant phenotype gene expression profile.

2. The method according to claim 1, wherein said at least three genes comprises: FAM110C, IGHG4 and KLF6.

3. The method according to claim 1, wherein said sample is a blood sample.

4. The method according to claim 1, wherein said expression product is selected from one or both of: a nucleic acid transcript and a protein.

5. The method of claim 4, wherein said expression product is a nucleic acid transcript and said evaluating step comprises performing one or more of the following: a RT-PCR assay, a microarray assay, and a Northern blot.

6. The method according to claim 1, wherein the expression level of BNC2, C1QC, CCL4, CYP1B1, FAM110C, GDEP, IGFL2, IGH@, IGHA2, IGHG4, IGJ, KLF6, NXF3, PRAMEF3, RLBP1L1, SHCBP1, SPC25, TFDP3, TNFRSF17, UHRF1 and VN1R2 is evaluated.

7. A method of managing immunosuppressive therapy treatment in a subject having an allograft, said method comprising:
(a) determining whether said subject has a graft tolerant phenotype according to claim 1; and
(b) managing future immunosuppressive therapy treatment in said subject based on said determining step (a).

8. A system for determining whether a subject who has received a renal allograft has a graft tolerant or a graft intolerant phenotype, said system comprising:
(a) a gene expression evaluation element for evaluating the level of expression of at least three genes in a sample from said subject to obtain a gene expression result, wherein said at least three genes are selected from the group consisting of: BNC2, CCL4, C1QC, CYP1B1, FAM110C, GDEP, IGJ, IGH@, IGHA2, IGHG4, IGFL2, KLF6, NXF3, PRAMEF3, RLBP1L1, SHCBP1, SPC25, TFDP3, TNFRSF17, UHRF1, and VN1R2; and
(b) a phenotype determination element for employing said gene expression element and determining whether said subject has a graft tolerant or a graft intolerant phenotype, the phenotype determination element comprising a reference expression profile for said at least three genes, wherein the phenotype determination element is obtained from a sample from a patient with a graft tolerant phenotype or a graft intolerant phenotype.

9. The system according to claim 8, wherein said gene expression evaluation element comprises a collection of reagents for assaying a sample for an expression product of each of said at least three genes.

10. The system according to claim 8, wherein said expression product of said at least three genes are selected from: a nucleic acid transcript and a protein.

11. The method according to claim 1, wherein said at least three genes comprises: CYP1B1, and BNC2.

12. The method according to claim 1, wherein said reference gene expression profile is from a subject having induced graft tolerance.

13. The method according to claim 1, wherein said comparing step comprises at least one of: comparing digital images of the expression profiles and comparing databases of expression data.

14. The method according to claim 3, wherein said blood sample is a peripheral blood lymphocyte sample.

15. The method according to claim 1, wherein said assessing is quantitative.

16. A method of determining whether a subject who has received a renal allograft has a graft tolerant or a graft intolerant phenotype comprising:
(a) obtaining a peripheral blood sample comprising a peripheral blood lymphocyte from a subject;
(b) evaluating the level of expression of at least three genes in said peripheral blood sample to obtain a gene expression result, wherein said at least three genes are selected from the group consisting of: BNC2, CCL4, C1QC, CYP1B1, FAM110C, GDEP, IGJ, IGH@, IGHA2, IGHG4, IGFL2, KLF6, NXF3, PRAMEF3, RLBP1L1, SHCBP1, SPC25, TFDP3, TNFRSF17, UHRF1, and VN1R2, and wherein said evaluating comprises:
extracting mRNA from said sample;
contacting said mRNA with a collection of reagents for assaying mRNA from each of said at least three genes;
assessing, using said collection of reagents, the amount of said mRNA from each of said at least three genes in said sample;
(c) comparing said gene expression result to at least one reference gene expression profile, wherein said reference gene expression profile is selected from: a graft tolerant phenotype gene expression profile and a graft intolerant phenotype gene expression profile; and
(d) determining that said subject has a graft tolerant phenotype based on said comparing when said gene expression result is similar to said graft tolerant phenotype gene expression profile and/or is dissimilar to said graft intolerant phenotype gene expression profile; or determining said subject has a graft intolerant phenotype based on said comparing when said gene expression result is dissimilar to said graft tolerant phenotype gene expression profile and/or is similar to said graft intolerant phenotype gene expression profile.

17. A method of treating a transplant recipient, said method comprising:
(a) evaluating whether said transplant recipient has a graft tolerant or a graft intolerant phenotype by using a gene expression result that was previously obtained from a quantitative determination of the nucleic acid expression levels of at least three genes in a sample from said a transplant recipient, wherein said at least at least three genes are selected from the group consisting of: BNC2, CCL4, C1QC, CYP1B1, FAM110C, GDEP, IGJ, IGH@, IGHA2, IGHG4, IGFL2, KLF6, NXF3, PRAMEF3, RLBP1L1, SHCBP1, SPC25, TFDP3, TNFRSF17, UHRF1, and VN1R2;
(b) comparing said previously obtained gene expression result to at least one reference gene expression profile, wherein said reference gene expression profile is selected from: a graft tolerant phenotype gene expression profile and a graft intolerant phenotype gene expression profile;
(c) determining that said transplant recipient has a graft tolerant phenotype based on said comparing when said gene expression result is similar to said graft tolerant phenotype gene expression profile and/or is dissimilar to said graft intolerant phenotype gene expression profile; or determining that said transplant recipient has a graft intolerant phenotype based on said comparing when said gene expression result is dissimilar to said graft tolerant phenotype gene expression profile and/or is similar to said graft intolerant phenotype gene expression profile; and
(d) treating said transplant recipient by decreasing a therapeutic regimen, maintaining a current therapeutic regimen, or increasing a therapeutic regimen based on the determining step (c).

18. The method according to claim 17, wherein said gene expression result was previously obtained by ordering a clinical test comprising the steps of:
(a) extracting mRNA from said sample;
(b) contacting said mRNA with a collection of reagents for assaying mRNA from each of said at least three genes; and
(c) assessing the amount of said mRNA from each of said at least three genes in said sample using said reagents to obtain said gene expression result.

19. The method according to claim 17, wherein said at least three genes comprises: FAM110C, IGHG4, and KLF6.

20. The method according to claim 17, wherein said at least three genes comprises: CYP1B1, KLF6, and BNC2.

* * * * *